United States Patent [19]

Kuwada et al.

[11] 4,150,139
[45] Apr. 17, 1979

[54] TRIAZOLOBENZAZEPINE DERIVATIVES

[75] Inventors: Yutaka Kuwada, Ashiya; Hiroyuki Tawada, Takatsuki, both of Japan

[73] Assignee: Takeda Chemical Industries, Ltd., Osaka, Japan

[21] Appl. No.: 821,623

[22] Filed: Aug. 3, 1977

[30] Foreign Application Priority Data

Aug. 6, 1976 [JP] Japan .................................. 51-94183
Feb. 18, 1977 [JP] Japan .................................. 52-17499
Feb. 18, 1977 [JP] Japan .................................. 52-17500

[51] Int. Cl.$^2$ ..................... A61K 31/55; C07D 487/04
[52] U.S. Cl. ............................... 424/269; 260/308 C; 260/340.9 R; 260/552 SC; 260/558 H
[58] Field of Search ..................... 260/308 R; 424/269

[56] References Cited

U.S. PATENT DOCUMENTS 4,002,638  1/1977  Kuwada et al. ................. 260/308 C

FOREIGN PATENT DOCUMENTS 2442987  3/1975  Fed. Rep. of Germany ...... 260/308 R

*Primary Examiner*—Alton D. Rollins
*Attorney, Agent, or Firm*—Burgess, Ryan and Wayne

[57] ABSTRACT

Novel triazolobenzazepine derivatives of the formula

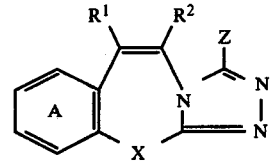

(wherein $R^1$ and $R^2$ are hydrogen or alkyl, X is

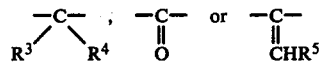

wherein $R^3$ and $R^4$ are hydrogen, alkyl, aryl or aralkyl, and $R^5$ is hydrogen or alkyl), Z is —$SR^6$, —$S(O)_nR^6$ or —$OR^7$ (wherein $R^6$ and $R^7$ are alkyl or aralkyl, and n is 1 or 2), and Ring A is unsubstituted or substituted with at least one of halogen, lower alkyl, lower alkoxy and trifluoromethyl, and their physiologically acceptable salts have excellent pharmacological activities and are useful as medicines such as muscle-relaxants, analgesics and antiinflammatory drugs.

61 Claims, No Drawings

TRIAZOLOBENZAZEPINE DERIVATIVES

This invention relates to novel and useful triazolobenzazepine derivatives.

The present inventors have succeeded in producing novel triazolobenzazepine derivatives of the formula

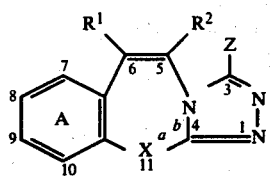

wherein $R^1$ and $R^2$ are hydrogen or alkyl, X is

(wherein $R^3$ and $R^4$ are hydrogen, alkyl, aryl or aralkyl, and $R^5$ is hydrogen or alkyl), Z is —$SR^6$, —$S(O)_nR^6$ or —$OR^7$ (wherein $R^6$ and $R^7$ are alkyl or aralkyl, and n is 1 or 2), and Ring A is unsubstituted or substituted with at least one of halogen, lower alkyl, lower alkoxy and trifluoromethyl, and their physiologically acceptable salts, which are useful as medicines such as muscle-relaxants, analgesics and antiinflammatory drugs.

Thus, the principal object of this invention is to provide the novel compound (I) and its salts which have the excellent pharmacological activities, and another object is to provide a pharmaceutical composition comprising the compound (I). A further object is to provide methods for production of the compound (I). Other objects will be made clear from the description and claims hereinafter.

Referring to the above formula (I), the alkyl groups designated by $R^1$, $R^2$, $R^3$, $R^4$, $R^5$, $R^6$ and $R^7$ may for example be lower alkyls, preferably of about 1 to 4 carbon atoms (e.g. methyl, ethyl, propyl, isopropyl, butyl, isobutyl, sec-butyl, tert-butyl, cyclopropylmethyl); the aralkyl groups $R^3$, $R^4$, $R^6$ and $R^7$ may be aliphatic chains of about 1 to 4 carbon atoms substituted with phenyl group (i.e. phenyl-$C_{1-4}$ alkyl), for example benzyl, phenethyl, α-phenylethyl, phenylpropyl, etc.; and the aryl groups $R^3$ and $R^4$ may for example be phenyl. Such aralkyl and aryl groups may each have an optional number of substituents in the substitutable positions on the benzene ring, said substituents being similar to the substitutents on Ring A which are hereinafter mentioned. The above $R^1$ and $R^2$ as well as $R^3$ and $R^4$ may be the same or different.

Where Ring A is substituted, the substituent or substituents may be halogens (e.g. fluorine, chlorine, bromine, iodine), lower alkyls, preferably of about 1 to 4 carbon atoms (e.g. methyl, ethyl, propyl, isopropyl, butyl), lower alkoxys, preferably of about 1 to 4 carbon atoms (e.g. methoxy, ethoxy, propoxy, isopropoxy, butoxy) and trifluoromethyl. Such substituents may be situated in substitutable positions of Ring A, and may be the same or different. The number of substituents may be up to 4 at the maximum.

The compound (I) of the present invention may be exemplified as follows:
3-Methylthio-11H-s-triazolo[3,4-b][3]benzazepine
3-Ethylthio-11H-s-triazolo[3,4-b][3]benzazepine
3-n-Propylthio-11H-s-triazolo[3,4-b][3]benzazepine
3-Isopropylthio-11H-s-triazolo[3,4-b][3]benzazepine
3-n-Butylthio-11H-s-triazolo[3,4-b][3]benzazepine
11-Methyl-3-methylthio-11H-s-triazolo[3,4-b][3]benzazepine
3-Ethylthio-11-methyl-11H-s-triazolo[3,4-b][3]benzazepine
3-Isopropylthio-11-methyl-11H-s-triazolo[3,4-b][3]benzazepine
11-Ethyl-3-methylthio-11H-s-triazolo[3,4-b][3]benzazepine
11-Ethyl-3-ethylthio-11H-s-triazolo[3,4-b][3]benzazepine
11-Ethyl-3-isopropylthio-11H-s-triazolo[3,4-b][3]benzazepine
11-Isopropyl-3-methylthio-11H-s-triazolo[3,4-b][3]benzazepine
3-Ethylthio-11-isopropyl-11H-s-triazolo[3,4-b][3]benzazepine
11-Butyl-3-methylthio-11H-s-triazolo[3,4-b][3]benzazepine
11,11-Dimethyl-3-methylthio-11H-s-triazolo[3,4-b][3]benzazepine
11,11-Dimethyl-3-ethylthio-11H-s-triazolo[3,4-b][3]benzazepine
11-Ethyl-11-methyl-3-methylthio-11H-s-triazolo[3,4-b][3]benzazepine
11-Benzyl-3-methylthio-11H-s-triazolo[3,4-b][3]benzazepine
3-Methylthio-11-phenyl-11H-s-triazolo[3,4-b][3]benzazepine
3-Ethylthio-11-phenyl-11H-s-triazolo[3,4-b][3]benzazepine
6-Methyl-3-methylthio-11H-s-triazolo[3,4-b][3]benzazepine
6-Ethyl-3-methylthio-11H-s-triazolo[3,4-b][3]benzazepine
5-Methyl-3-methylthio-11H-s-triazolo[3,4-b][3]benzazepine
5-Ethyl-3-methylthio-11H-s-triazolo[3,4-b][3]benzazepine
5-Isopropyl-3-methylthio-11H-s-triazolo[3,4-b][3]benzazepine
5,11-Dimethyl-3-methylthio-11H-s-triazolo[3,4-b][3]benzazepine
3-Methylthio-5,11,11-trimethyl-11H-s-triazolo[3,4-b][3]benzazepine
5-Methyl-3-methylthio-11-phenyl-11H-s-triazolo[3,4-b][3]benzazepine
8-Chloro-3-methylthio-11H-s-triazolo[3,4-b][3]benzazepine
9-Chloro-3-methylthio-11H-s-triazolo[3,4-b][3]benzazepine
10-Chloro-3-methylthio-11H-s-triazolo[3,4-b][3]benzazepine
8-Bromo-3-methylthio-11H-s-triazolo[3,4-b][3]benzazepine
8-Methyl-3-methylthio-11H-s-triazolo[3,4-b][3]benzazepine
8-Methoxy-3-methylthio-11H-s-triazolo[3,4-b][3]benzazepine
9-Methoxy-3-methylthio-11H-s-triazolo[3,4-b][3]benzazepine
8,9-Dimethoxy-3-methylthio-11H-s-triazolo[3,4-b][3]benzazepine
3-Methylthio-8-trifluoromethyl-11H-s-triazolo[3,4-b][3]benzazepine
11-Methylene-3-methylthio-11H-s-triazolo[3,4-b][3]benzazepine 11-Ethylidene-3-methylthio-11H-s-triazolo[3,4-b][3]benzazepine
3-Methylthio-11-propylidene-11H-s-triazolo[3,4-b][3]benzazepine
8-Chloro-11-methylene-3-methylthio-11H-s-triazolo[3,4-b][3]benzazepine
11-Methylene-8-methyl-3-methylthio-11H-s-triazolo[3,4-b][3]benzazepine
11-Methylene-8-methoxy-3-methylthio-11H-s-triazolo[3,4-b][3]benzazepine
11-Methylene-9-methoxy-3-methylthio-11H-s-triazolo[3,4-b][3]benzazepine
8,9-Dimethoxy-11-methylene-3-methylthio-11H-s-triazolo[3,4-b][3]benzazepine
3-Methylthio-11H-s-triazolo[3,4-b][3]benzazepin-11-one
3-Ethylthio-11H-s-triazolo[3,4-b][3]benzazepin-11-one
3-Isopropylthio-11H-s-triazolo[3,4-b][3]benzazepin-11-one
8-Chloro-3-methylthio-11H-s-triazolo[3,4-b][3]benzazepin-11-one
8-Methyl-3-methylthio-11H-s-triazolo[3,4-b][3]benzazepin-11-one
8-Methoxy-3-methylthio-11H-s-triazolo[3,4-b][3]benzazepin-11-one
9-Methoxy-3-methylthio-11H-s-triazolo[3,4-b][3]benzazepin-11-one
3-Methylthio-8-trifluoromethyl-11H-s-triazolo[3,4-b][3]benzazepin-11-one
3-Methylsulfinyl-11H-s-triazolo[3,4-b][3]benzazepine
3-Methylsulfonyl-11H-s-triazolo[3,4-b][3]benzazepine
3-Ethylsulfinyl-11H-s-triazolo[3,4-b][3]benzazepine
3-Ethylsulfonyl-11H-s-triazolo[3,4-b][3]benzazepine
3-Propylsulfinyl-11H-s-triazolo[3,4-b][3]benzazepine
3-Propylsulfonyl-11H-s-triazolo[3,4-b][3]benzazepine
3-Isopropylsulfinyl-11H-s-triazolo[3,4-b][3]benzazepine
3-Isopropylsulfonyl-11H-s-triazolo[3,4-b][3]benzazepine
3-Butylsulfinyl-11H-s-triazolo[3,4-b][3]benzazepine
3-Butylsulfonyl-11H-s-triazolo[3,4-b][3]benzazepine
11-Methyl-3-methylsulfinyl-11H-s-triazolo[3,4-b][3]benzazepine
11-Methyl-3-methylsulfonyl-11H-s-triazolo[3,4-b][3]benzazepine
3-Ethylsulfinyl-11-methyl-11H-s-triazolo[3,4-b][3]benzazepine
3-Ethylsulfonyl-11-methyl-11H-s-triazolo[3,4-b][3]benzazepine
3-Isopropylsulfonyl-11-methyl-11H-s-triazolo[3,4-b][3]benzazepine
11-Ethyl-3-methylsulfinyl-11H-s-triazolo[3,4-b][3]benzazepine
11-Ethyl-3-methylsulfonyl-11H-s-triazolo[3,4-b][3]benzazepine
11-Ethyl-3-ethylsulfinyl-11H-s-triazolo[3,4-b][3]benzazepine
11-Ethyl-3-ethylsulfonyl-11H-s-triazolo[3,4-b][3]benzazepine
3-Methylsulfinyl-11-propyl-11H-s-triazolo[3,4-b][3]benzazepine
3-Methylsulfonyl-11-propyl-11H-s-triazolo[3,4-b][3]benzazepine
11-Isopropyl-3-methylsulfinyl-11H-s-triazolo[3,4-b][3]benzazepine
11-Isopropyl-3-methylsulfonyl-11H-s-triazolo[3,4-b][3]benzazepine
11,11-Dimethyl-3-methylsulfinyl-11H-s-triazolo[3,4-b][3]benzazepine
11,11-Dimethyl-3-methylsulfonyl-11H-s-triazolo[3,4-b][3]benzazepine
11,11-Dimethyl-3-ethylsulfinyl-11H-s-triazolo[3,4-b][3]benzazepine
11,11-Dimethyl-3-ethylsulfonyl-11H-s-triazolo[3,4-b][3]benzazepine
11-Ethyl-11-methyl-3-methylsulfinyl-11H-s-triazolo[3,4-b][3]benzazepine
11-Ethyl-11-methyl-3-methylsulfonyl-11H-s-triazolo[3,4-b][3]benzazepine
11-Benzyl-3-methylsulfinyl-11H-s-triazolo[3,4-b][3]benzazepine
11-Benzyl-3-methylsulfonyl-11H-s-triazolo[3,4-b][3]benzazepine
3-Methylsulfinyl-11-phenyl-11H-s-triazolo[3,4-b][3]benzazepine
3-Methylsulfonyl-11-phenyl-11H-s-triazolo[3,4-b][3]benzazepine
3-Ethylsulfinyl-11-phenyl-11H-s-triazolo[3,4-b][3]benzazepine
3-Ethylsulfonyl-11-phenyl-11H-s-triazolo[3,4-b][3]benzazepine
6-Methyl-3-methylsulfinyl-11H-s-triazolo[3,4-b][3]benzazepine
6-Methyl-3-methylsulfonyl-11H-s-triazolo[3,4-b][3]benzazepine
5-Methyl-3-methylsulfinyl-11H-s-triazolo[3,4-b][3]benzazepine
5-Methyl-3-methylsulfonyl-11H-s-triazolo[3,4-b][3]benzazepine
5-Ethyl-3-methylsulfinyl-11H-s-triazolo[3,4-b][3]benzazepine
5-Ethyl-3-methylsulfonyl-11H-s-triazolo[3,4-b][3]benzazepine
5,11-Dimethyl-3-methylsulfinyl-11H-s-triazolo[3,4-b][3]benzazepine
5,11-Dimethyl-3-methylsulfonyl-11H-s-triazolo[3,4-b][3]benzazepine
3-Methylsulfinyl-5,11,11-trimethyl-11H-s-triazolo[3,4-b][3]benzazepine
3-Methylsulfonyl-5,11,11-trimethyl-11H-s-triazolo[3,4-b][3]benzazepine
5-Methyl-3-methylsulfinyl-11-phenyl-11H-s-triazolo[3,4-b][3]benzazepine
5-Methyl-3-methylsulfonyl-11-phenyl-11H-s-triazolo[3,4-b][3]benzazepine
8-Chloro-3-methylsulfinyl-11H-s-triazolo[3,4-b][3]benzazepine
8-Chloro-3-methylsulfonyl-11H-s-triazolo[3,4-b][3]benzazepine
9-Chloro-3-methylsulfinyl-11H-s-triazolo[3,4-b][3]benzazepine
9-Chloro-3-methylsulfonyl-11H-s-triazolo[3,4-b][3]benzazepine
10-Chloro-3-methylsulfinyl-11H-s-triazolo[3,4-b][3]benzazepine
10-Chloro-3-methylsulfonyl-11H-s-triazolo[3,4-b][3]benzazepine
8-Bromo-3-methylsulfinyl-11H-s-triazolo[3,4-b][3]benzazepine
8-Bromo-3-methylsulfonyl-11H-s-triazolo[3,4-b][3]benzazepine
8-Methyl-3-methylsulfinyl-11H-s-triazolo[3,4-b][3]benzazepine
8-Methyl-3-methylsulfonyl-11H-s-triazolo[3,4-b][3]benzazepine
8-Methoxy-3-methylsulfinyl-11H-s-triazolo[3,4-b][3]benzazepine 8-Methoxy-3-methylsulfonyl-11H-s-triazolo[3,4-b][3]benzazepine
9-Methoxy-3-methylsulfinyl-11H-s-triazolo[3,4-b][3]benzazepine
9-Methoxy-3-methylsulfonyl-11H-s-triazolo[3,4-b][3]benzazepine
8,9-Dimethoxy-3-methylsulfinyl-11H-s-triazolo[3,4-b][3]benzazepine
8,9-Dimethoxy-3-methylsulfonyl-11H-s-triazolo[3,4-b][3]benzazepine
3-Methylsulfinyl-8-trifluoromethyl-11H-s-triazolo[3,4-b][3]benzazepine
3-Methylsulfonyl-8-trifluoromethyl-11H-s-triazolo[3,4-b][3]benzazepine
11-Methylene-3-methylsulfinyl-11H-s-triazolo[3,4-b][3]benzazepine
11-Methylene-3-methylsulfonyl-11H-s-triazolo[3,4-b][3]benzazepine
3-Ethylsulfinyl-11-methylene-11H-s-triazolo[3,4-b][3]benzazepine
3-Ethylsulfonyl-11-methylene-11H-s-triazolo[3,4-b][3]benzazepine
11-Ethylidene-3-methylsulfinyl-11H-s-triazolo[3,4-b][3]benzazepine
11-Ethylidene-3-methylsulfonyl-11H-s-triazolo[3,4-b][3]benzazepine
3-Methylsulfinyl-11-propylidene-11H-s-triazolo[3,4-b][3]benzazepine
3-Methylsulfonyl-11-propylidene-11H-s-triazolo[3,4-b][3]benzazepine
8-Chloro-11-methylene-3-methylsulfinyl-11H-s-triazolo[3,4-b][3]benzazepine
8-Chloro-11-methylene-3-methylsulfonyl-11H-s-triazolo[3,4-b][3]benzazepine
11-Methylene-8-methyl-3-methylsulfinyl-11H-s-triazolo[3,4-b][3]benzazepine
11-Methylene-8-methyl-3-methylsulfonyl-11H-s-triazolo[3,4-b][3]benzazepine
11-Methylene-8-methoxy-3-methylsulfinyl-11H-s-triazolo[3,4-b][3]benzazepine
11-Methylene-8-methoxy-3-methylsulfonyl-11H-s-triazolo[3,4-b][3]benzazepine
11-Methylene-9-methoxy-3-methylsulfinyl-11H-s-triazolo[3,4-b][3]benzazepine
11-Methylene-9-methoxy-3-methylsulfonyl-11H-s-triazolo[3,4-b][3]benzazepine
8,9-Dimethoxy-11-methylene-3-methylsulfinyl-11H-s-triazolo[3,4-b][3]benzazepine
8,9-Dimethoxy-11-methylene-3-methylsulfonyl-11H-s-triazolo[3,4-b][3]benzazepine
3-Methylsulfinyl-11H-s-triazolo[3,4-b][3]benzazepin-11-one
3-Methylsulfonyl-11H-s-triazolo[3,4-b][3]benzazepin-11-one
3-Ethylsulfinyl-11H-s-triazolo[3,4-b][3]benzazepin-11-one
3-Ethylsulfonyl-11H-s-triazolo[3,4-b][3]benzazepin-11-one
3-Isopropylsulfinyl-11H-s-triazolo[3,4-b][3]benzazepin-11-one
3-Isopropylsulfonyl-11H-s-triazolo[3,4-b][3]benzazepin-11-one
8-Chloro-3-methylsulfinyl-11H-s-triazolo[3,4-b][3]benzazepin-11-one
8-Chloro-3-methylsulfonyl-11H-s-triazolo[3,4-b][3]benzazepin-11-one
8-Methyl-3-methylsulfinyl-11H-s-triazolo[3,4-b][3]benzazepin-11-one
8-Methyl-3-methylsulfonyl-11H-s-triazolo[3,4-b][3]benzazepin-11-one
8-Methoxy-3-methylsulfinyl-11H-s-triazolo[3,4-b][3]benzazepin-11-one
8-Methoxy-3-methylsulfonyl-11H-s-triazolo[3,4-b][3]benzazepin-11-one
9-Methoxy-3-methylsulfinyl-11H-s-triazolo[3,4-b][3]benzazepin-11-one
9-Methoxy-3-methylsulfonyl-11H-s-triazolo[3,4-b][3]benzazepin-11-one
3-Methylsulfinyl-8-trifluoromethyl-11H-s-triazolo[3,4-b][3]benzazepin-11-one
3-Methylsulfonyl-8-trifluoromethyl-11H-s-triazolo[3,4-b][3]benzazepin-11-one
3-Benzylsulfinyl-11H-s-triazolo[3,4-b][3]benzazepine
3-Benzylsulfonyl-11H-s-triazolo[3,4-b][3]benzazepine
3-Methoxy-11H-s-triazolo[3,4-b][3]benzazepine
3-Ethoxy-11H-s-triazolo[3,4-b][3]benzazepine
3-Propoxy-11H-s-triazolo[3,4-b][3]benzazepine
3-Isopropoxy-11H-s-triazolo[3,4-b][3]benzazepine
3-Butoxy-11H-s-triazolo[3,4-b][3]benzazepine
3-Benzyloxy-11H-s-triazolo[3,4-b][3]benzazepine
3-Phenethyloxy-11H-s-triazolo[3,4-b][3]benzazepine
3-Methoxy-11-methyl-11H-s-triazolo[3,4-b][3]benzazepine
3-Ethoxy-11-methyl-11H-s-triazolo[3,4-b][3]benzazepine
11-Methyl-3-isopropoxy-11H-s-triazolo[3,4-b][3]benzazepine
11-Ethyl-3-methoxy-11H-s-triazolo[3,4-b][3]benzazepine
3-Ethoxy-11-ethyl-11H-s-triazolo[3,4-b][3]benzazepine
3-Methoxy-11-propyl-11H-s-triazolo[3,4-b][3]benzazepine
3-Ethoxy-11-propyl-11H-s-triazolo[3,4-b][3]benzazepine
11-Butyl-3-methoxy-11H-s-triazolo[3,4-b][3]benzazepine
11,11-Dimethyl-3-methoxy-11H-s-triazolo[3,4-b][3]benzazepine
11,11-Dimethyl-3-ethoxy-11H-s-triazolo[3,4-b][3]benzazepine
11-Ethyl-3-methoxy-11-methyl-11H-s-triazolo[3,4-b][3]benzazepine
11-Benzyl-3-methoxy-11H-s-triazolo[3,4-b][3]benzazepine
11-Benzyl-3-ethoxy-11H-s-triazolo[3,4-b][3]benzazepine
3-Methoxy-11-phenyl-11H-s-triazolo[3,4-b][3]benzazepine
3-Ethoxy-11-phenyl-11H-s-triazolo[3,4-b][3]benzazepine
3-Methoxy-6-methyl-11H-s-triazolo[3,4-b][3]benzazepine
3-Ethoxy-6-methyl-11H-s-triazolo[3,4-b][3]benzazepine
3-Ethoxy-6-ethyl-11H-s-triazolo[3,4-b][3]benzazepine
3-Methoxy-5-methyl-11H-s-triazolo[3,4-b][3]benzazepine
3-Ethoxy-5-methyl-11H-s-triazolo[3,4-b][3]benzazepine
5-Ethyl-3-methoxy-11H-s-triazolo[3,4-b][3]benzazepine
3-Ethoxy-5-ethyl-11H-s-triazolo[3,4-b][3]benzazepine
5,11-Dimethyl-3-ethoxy-11H-s-triazolo[3,4-b][3]benzazepine
3-Ethoxy-5-methyl-11-phenyl-11H-s-triazolo[3,4-b][3]benzazepine
8-Chloro-3-methoxy-11H-s-triazolo[3,4-b][3]benzazepine
8-Chloro-3-ethoxy-11H-s-triazolo[3,4-b][3]benzazepine 9-Chloro-3-ethoxy-11H-s-triazolo[3,4-b][3]benzazepine
10-Chloro-3-ethoxy-11H-s-triazolo[3,4-b][3]benzazepine
8-Bromo-3-ethoxy-11H-s-triazolo[3,4-b][3]benzazepine
3-Methoxy-8-methyl-11H-s-triazolo[3,4-b][3]benzazepine
3-Ethoxy-8-methyl-11H-s-triazolo[3,4-b][3]benzazepine
3,8-Dimethoxy-11H-s-triazolo[3,4-b][3]benzazepine
3-Ethoxy-8-methoxy-11H-s-triazolo[3,4-b][3]benzazepine
3,9-Dimethoxy-11H-s-triazolo[3,4-b][3]benzazepine
3-Ethoxy-9-methoxy-11H-s-triazolo[3,4-b][3]benzazepine
8,9-Dimethoxy-3-ethoxy-11H-s-triazolo[3,4-b][3]benzazepine
3-Ethoxy-8-trifluoromethyl-11H-s-triazolo[3,4-b][3]benzazepine
3-Methoxy-11-methylene-11H-s-triazolo[3,4-b][3]benzazepine
3-Ethoxy-11-methylene-11H-s-triazolo[3,4-b][3]benzazepine
11-Ethylidene-3-methoxy-11H-s-triazolo[3,4-b][3]benzazepine
3-Methoxy-11-propylidene-11H-s-triazolo[3,4-b][3]benzazepine
8-Chloro-3-methoxy-11-methylene-11H-s-triazolo[3,4-b][3]benzazepine
8-Chloro-11-ethylidene-3-methoxy-11H-s-triazolo[3,4-b][3]benzazepine
3-Methoxy-8-methyl-11-methylene-11H-s-triazolo[3,4-b][3]benzazepine
11-Ethylidene-3-methoxy-8-methyl-11H-s-triazolo[3,4-b][3]benzazepine
3,8-Dimethoxy-11-methylene-11H-s-triazolo[3,4-b][3]benzazepine
3,9-Dimethoxy-11-methylene-11H-s-triazolo[3,4-b][3]benzazepine
3-Methoxy-11H-s-triazolo[3,4-b][3]benzazepin-11-one
3-Ethoxy-11H-s-triazolo[3,4-b][3]benzazepin-11-one
3-Ethoxy-6-methyl-11H-s-triazolo[3,4-b][3]benzazepin-11-one
8-Chloro-3-methoxy-11H-s-triazolo[3,4-b][3]benzazepin-11-one
8-Chloro-3-ethoxy-11H-s-triazolo[3,4-b][3]benzazepin-11-one
3-Ethoxy-8-methyl-11H-s-triazolo[3,4-b][3]benzazepin-11-one
3-Ethoxy-8-methoxy-11H-s-triazolo[3,4-b][3]benzazepin-11-one The compound (I) of the present invention can be produced, for example, by the following Processes A, B, C, D, E and/or F.

Process A

Among the compounds (I), a compound of the formula

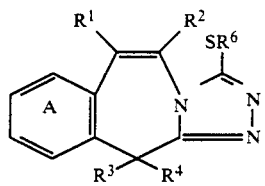

(Ia)

wherein all the symbols are defined as above, can be produced by subjecting a compound of the formula

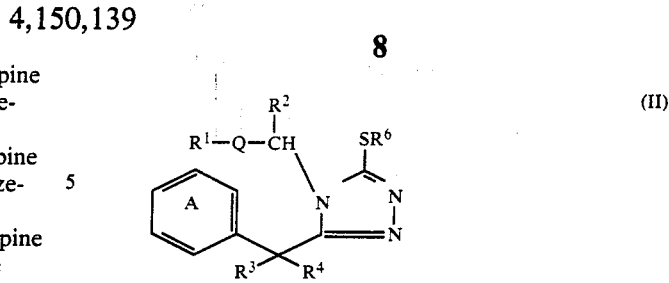

(II)

wherein Q is carbonyl or its acetal group, and the other symbols are as defined as above, to intramolecular cyclization.

Referring to the above formula (II), the acetal group Q is represented by the formula

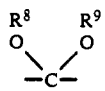

wherein $R^8$ and $R^9$ are lower alkyl of about 1 to 3 carbon atoms (e.g. methyl, ethyl, propyl, etc.), or $R^8$ and $R^9$, taken together, form a lower alkylene group of about 2 to 4 carbon atoms (e.g. ethylene, propylene, etc.).

The cyclization reaction of this process from the compound (II) to the compound (Ia) normally takes place in the presence of an acid catalyst. As examples of said acid catalyst may be mentioned mineral acids (e.g. hydrochloric acid, hydrobromic acid, sulfuric acid, phosphoric acid, perchloric acid), Lewis acids (e.g. aluminum chloride, titanium trichloride, tin trichloride, boron trifluoride), polyphosphoric acid and polyphosphoric acid esters. Generally, at least one molecular equivalent of such acid is employed with respect to the compound (II). This reaction is normally conducted in a solvent. The solvent may be either any of the acids mentioned above for the cyclization reaction, in which case the acid plays a dual role of cyclizing agent and solvent, or any other inert solvent that will not interfere with the reaction. Thus, normally aromatic hydrocarbons (e.g. benzene, toluene, xylene) and halogenated aliphatic hydrocarbons (e.g. dichloromethane, dichloroethane, chloroform, carbon tetrachloride, tetrachloroethane may be employed. The reaction is normally conducted at an appropriate temperature between −10° C. and +200° C., it being generally advantageous to carry out the reaction in the neighborhood at room temperature. If necessary, an elevated temperature may be employed.

Process B

The compound (Ia) can be produced by reacting a compound of the formula

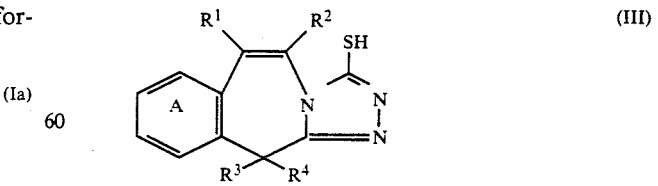

(III)

wherein all the symbols are defined as above, with an alkylating or aralkylating agent.

The reaction of this process from the compound (III) to the compound (Ia) is conducted by means of an alkylating or aralkylating agent. Such alkylating or aralkylating agent may be any reagent of the type, only if it is able to introduce $R^6$ into the mercapto group of the compound (III). Normally, a sulfuric acid dialkyl ester or sulfuric acid diaralkyl ester of the formula $$(R^6)_2SO_4 \quad (IVa)$$

[wherein $R^6$ is defined as above] or an alkyl halide or aralkyl halide of the formula $$R^6X' \quad (IVb)$$

[wherein $R^6$ is as previously defined; $X'$ is a halogen atom similar to the substituent on Ring A] is preferably employed. This reaction need not always be conducted in the presence of a solvent but said alkylating or aralkylating agent may be employed in excess so that it may also act as a solvent. Normally, however, this reaction is conducted with advantage in a suitable solvent such as an alcohol (e.g. methanol, ethanol), hydrocarbon (e.g. benzene, toluene, xylene), dimethylformamide or dimethylsulfoxide. Generally, satisfactory results are obtained if the mercapto group of compound (III) is first converted to an alkali metal salt prior to the alkylation or aralkylation according to this invention. To prepare such an alkali metal salt of compound (III), one of alkali metal hydroxides (e.g. sodium hydroxide, potassium hydroxide), alkali metal alkoxides (e.g. sodium methoxide, potassium methoxide, sodium ethoxide, potassium ethoxide, potassium tert-butoxide), alkali metal amides (e.g. sodium amide, potassium amide), alkali metal hydrides (e.g. sodium hydride, lithium hydride), etc. may be employed. The amount of such alkali metal compound is normally about 1 to 5 mole equivalents based on compound (III). Normally the amount of said alkylating or aralkylating agent is preferably 1 to 5 equivalents based on compound (III). Whilst this reaction normally proceeds at room temperature or lowered temperature, the reaction may be hastened by conducting it at a suitable elevated temperature.

Process C

Among the compound (I), a compound of the formula

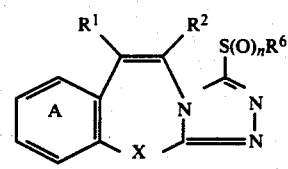
(Ib)

wherein all the symbols are defined as above, can be produced by oxidizing a compound of the formula

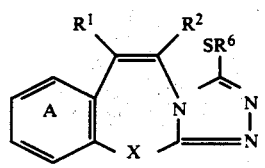
(Ia')

wherein all the symbols are defined as above.

The reaction of this process is accomplished by means of an oxidizing agent. This oxidizing agent may be any reagent capable of oxidizing a thioether group and, normally, hydrogen peroxide, organic per-acids (e.g. performic acid, peracetic acid, perbenzoic acid, m-chloroperbenzoic acid), permanganic acid salts (e.g. potassium permanganate, sodium permanganate), halogens (e.g. chlorine, bromine), active organic halogen compounds (N-bromosuccinimide, N-chlorosuccinimide), etc. may be successfully employed. This reaction is normally conducted with advantage in a suitable solvent such as water, alcohol (e.g. methanol, ethanol, propanol), organic carboxylic acids (e.g. formic acid, acetic acid), halogenated hydrocarbons (e.g. dichloromethane, chloroform), aromatic hydrocarbons (e.g. benzene, toluene, xylene), tetrahydrofuran, dioxane, etc.

There are cases in which this reaction may be more advantageously conducted in the presence of an acid or a base, depending upon the type of oxidizing agent. The acid may normally be a mineral acid (e.g. hydrochloric acid, hydrobromic acid, sulfuric acid, phosphoric acid) or an organic acid (e.g. formic acid, acetic acid), and the base may for example be an alkali hydroxide (e.g. sodium hydroxide, potassium hydroxide) or a tertiary amine (e.g. trimethylamine, triethylamine, pyridine).

In this reaction, by selecting the proper type and amount of oxidizing agent, reaction temperature and other reaction parameters, either the compound of formula (Ib) wherein n is 1 or the compound (Ib) wherein n is 2 may be selectively produced. Normally, if the reaction is conducted at a temperature not over room temperature using the oxidizing agent in a proportion of one mole equivalent of active oxygen per mole of compound (Ia'), the compound (Ib) in which n is 1 is usually produced, while the compound (Ib) in which n is 2 is normally produced when an excess of the oxidizing agent is employed.

This reaction is normally conducted at temperature between $-20°$ C. and $+150°$ C. Generally, in many instances, the reaction proceeds smoothly in the neighborhood of room temperature and, if necessary, the reaction may be carried out at an elevated or lowered temperature.

Process D

Among the compound (I), a compound of the formula

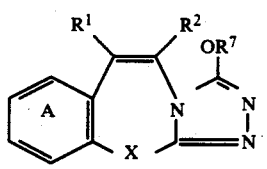
(Ic)

wherein all the symbols are defined as above, can be produced by reacting a compound of the formula

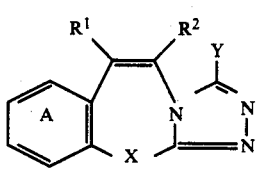
(V)

wherein Y is halogen or $-S(O)_nR^6$ (wherein $R^6$ and n are defined as above), and the other symbols are defined as above, with an alcoholate of the formula $$R^7-OM \quad (VI)$$

wherein M is alkali metal and $R^7$ is defined as above.

Referring to the formula (V), the halogen atom Y may for example be chlorine, bromine or iodine. The alkali metal M may for example be sodium or potassium.

In this process, the compound (V) is reacted with the compound (VI) to produce the contemplated compound (Ic). This reaction is normally conducted in the presence of a solvent. The solvent may be any solvent that will not interfere with the reaction and, preferably, is the alcohol having the same R-group as that of the reactant alcoholate (VI). Thus, for example, methanol, ethanol, propanol, isopropanol, butanol, sec-butanol, tert-butanol, etc. may be mentioned. Other solvents inert to the reaction such as aromatic hydrocarbons (e.g. benzene, toluene, xylene) or ethers (e.g. diethyl ether, isopropyl ether, tetrahydrofuran, dioxane) may also be employed. Normally, each mole of compound (V) is reacted with no less than one mole to about 10 moles of compound (VI). The reaction is normally conducted at a temperature between $-10°$ C. and $+200°$ C. and, generally, is desirably conducted around the boiling point of the solvent employed.

Process E

Among the compound (I), a compound of the formula

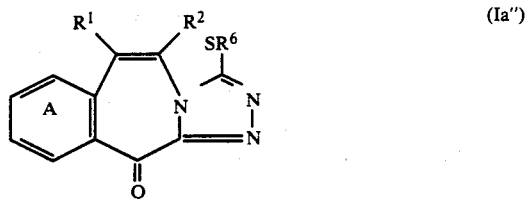

wherein all the symbols are defined as above, can be produced by oxidizing the compound of the formula (Ia) wherein $R^3$ and $R^4$ are hydrogen.

The reaction of this process is accomplished by means of an oxidizing agent such as selenium dioxide.

Process F

Among the compound (I), a compound of the formula

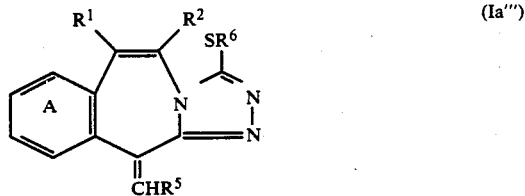

wherein all the symbols are defined as above, can be produced by reacting the compound of the formula (Ia) wherein $R^3$ and $R^4$ are hydrogen, with an aldehyde of the formula $R^5.CHO$ (wherein $R^5$ is defined as above).

This reaction is generally carried out in the presence of a base such as alkali hydroxide (e.g. sodium or potassium hydroxide), triethylamine or trimethylbenzylammonium hydroxide).

The compounds (Ia), (Ia''), (Ia'''), (Ib) and (Ic), i.e., the contemplated compound (I) produced in the above processes can be isolated as a product of desired purity grade by separation and purification procedures known per se, such as concentration, extraction, chromatography, recrystallization, etc. The compound (I) may also be recovered as a physiologically acceptable salt such as a mineral acid salt by treating with the corresponding mineral acid (e.g. hydrochloric acid, hydrobromic acid, sulfuric acid).

The compound (I) and its salt obtainable in the above manner have muscle-relaxant, analgesic, antiinflammatory, antipyretic and other activities in animals and, particularly, in mammals (e.g. human being, dog, rabbit, rat and mouse) and are of value as muscle-relaxants, analgesics, antiinflammatory drugs and other medicaments for the treatment and improvement of myalgia and other diseases. When the compound (I) or salt thereof is employed as such a drug, it can be safely administered, by the oral or parenteral route, either as it is or in admixture with pharmaceutically acceptable inert carriers, in such suitable dosage forms as powders, granules, tablets, capsules, injections, suppositories, etc. Whilst the proper dosage of compound (I) or salt thereof depends upon such factors as the route of administration, symptoms and the degree of disease, where the compound (I) is used as analgesics for the treatment of myalgia, it is normally administered at a daily dose of about 10 mg to about 250 mg per adult human by the oral route.

The analgesic effects of some representative compounds (I) are set forth below in Table I.

Table 1

Analgesic Effect

[mice, acetic acid-writhing method]

| Compounds | $ED_{50}$ (95% C.L.*) mg/kg,P.O.** |
|---|---|
| (I')Z = $SCH_3$ | 10.5(6.3–17.3) |
| (I')Z = $SOCH_3$ | 10.3(5.6–19.0) |

*C.L.: confidential limit
**P.O.: per os

The compound (I) is not only useful per se as a drug, but also is of value as intermediate for the synthesis of medicine. For example, the compound (Ia), (Ia''), (Ia''') or (Ib) may be converted to a 3-keto compound (VII) by treating with acid or alkali, or to a compound (VIII) by means of a desulfurizing agent (e.g. Raney nickel), as illustrated in the following reaction scheme:

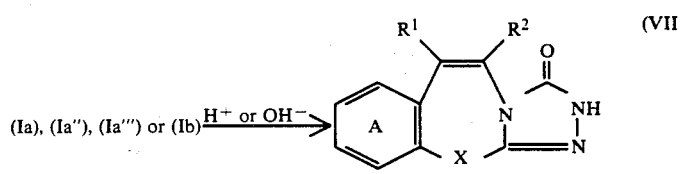

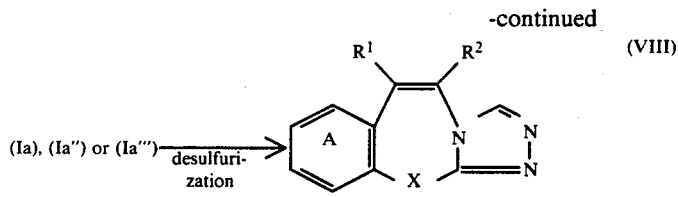

[wherein all the symbols are defined as above].

The above compounds (VII) and (VIII) have analgesic, muscle-relaxant, antiinflammatory and other pharmacological activities, and are of value as medicines such as analgesics, muscle relaxants, etc. [cf. West German Patent Application Laid Open to the Public (OLS) No. 2442987].

The starting compounds in Processes A, B and D mentioned hereinbefore can be produced, for example, as follows:

(a)

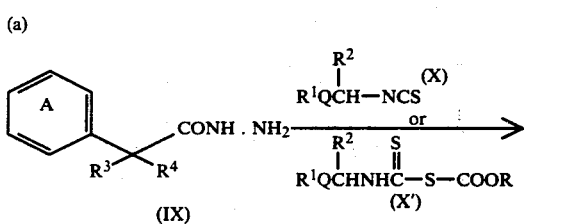

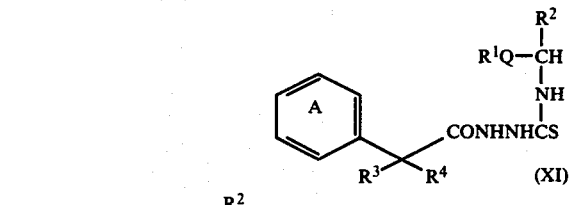

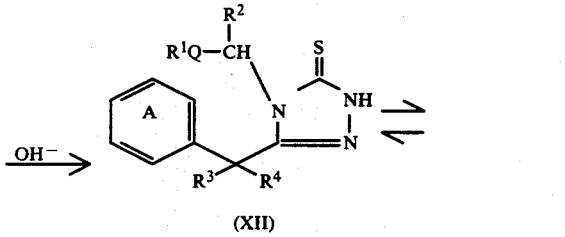

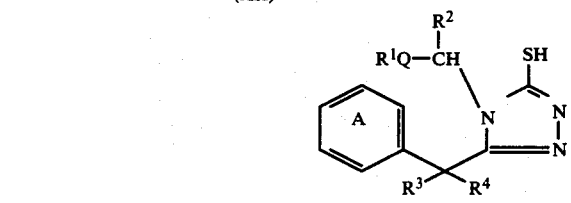

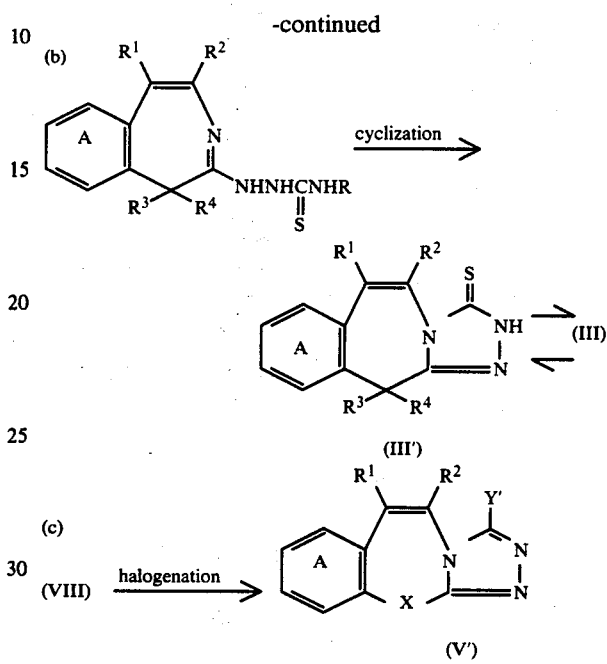

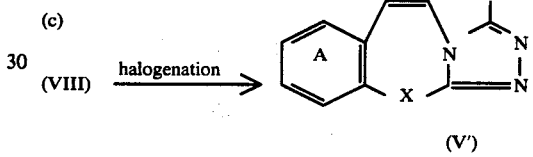

[wherein R is lower alkyl, X' and Y' are halogen, and the other symbols are defined as above].

As shown in the reaction scheme (a), a phenylacetic acid hydrazide derivative of formula (IX) is reacted with an isothiocyanate compound of formula (X) or a mixed anhydride of dithiocarbamic acid-carbonic acid ester of formula (X'). This reaction is conducted either in the absence of a solvent or, normally, in the presence of a solvent (e.g. water, alcohols, tetrahydrofuran, benzene), at a temperature from room temperature to the boiling point of the solvent used. By this reaction is obtained a thiosemicarbazide derivative of formula (XI). Compound (XI) may be isolated but, normally, the reaction mixture containing (XI) is subjected to the next cyclization reaction. Thus, compound (XI) undergoes cyclization on treatment with alkali. This cyclization is normally conducted using a metal hydroxide (e.g. sodium hydroxide, potassium hydroxide) with an aqueous solvent or an alcoholate (e.g. the methoxide and ethoxide of sodium or potassium) with the corresponding alcohol. The reaction proceeds at temperatures from room temperature to the boiling point of the solvent employed. The reaction gives triazole derivative (XII) and its tautomer (XII').

The compound (XII) or (XII') yields the starting compound (II) upon reaction with an alkyl halide (or aralkyl halide) in the presence of an alkali base (e.g. sodium hydroxide, potassium hydroxide, sodium methoxide, potassium methoxide, sodium ethoxide, potassium ethoxide), normally in a solvent which is preferably an anhydrous solvent such as alcohol (e.g. methanol, ethanol).

The starting compound (III) can be synthesized, for example, by the method disclosed in West German Patent Application Laid Open to the Public (OLS) No. 2442987, as shown in the reaction scheme (b). It should be understood that compound (III') is a tautomeric form of (III).

The compound (V'), i.e., the compound (V) wherein Y is halogen, can be obtained by reacting the compound (VIII) with a halogenating agent (e.g. chlorine, bromine, N-bromosuccinimide), as shown in the reaction scheme (c).

The following reference and working examples are intended to illustrate this invention in further detail and should be no means be construed as limiting the scope of the invention.

Throughout the forgoing description as well as in the following examples, "g", "mg", "l", "ml" and "° C." respectively refer to "gram(s)", "milligram(s)", "liter(s)", "milliliter(s)" and "degree(s) centigrade", and "NMR", "m.p." and "calcd." respectively mean "nuclear magnetic resonance spectrum", "melting point" and "calculated".

REFERENCE EXAMPLE 1

A mixture of 2.3 g of phenylacetic acid hydrazide and 2.8 g of 2,2-diethoxyethyl isothiocyanate in 30 ml of ethanol was heated on a water bath at 90° C. for 5 minutes and, then, allowed to stand at room temperature for 30 minutes. The solvent was evaporated and the residue was treated with n-hexane. The crystals thus obtained of 4-(2,2-diethoxyethyl)-1-phenylacetylthiosemicarbazide were recrystallized from ethanol-n-hexane and aqueous ethanol in the order mentioned. The above procedure yielded colorless needles melting at 93°-94° C.

Elemental analysis, for $C_{15}H_{23}N_3O_3S$; Calcd. C, 55.36; H, 7.12; N, 12.91; Found C, 55.45; H, 7.26; N, 12.61.

REFERENCE EXAMPLE 2

To 20 ml of a 2N-aqueous solution of potassium hydroxide was added 3.25 g of the 4-(2,2-diethoxyethyl)-1-phenylacetylthiosemicarbazide prepared in Reference Example 1. The mixture was heated on a water bath at 95° C. for 15 minutes and, then under ice-cooling, 2.4 g of ammonium chloride was added. The resultant 3-benzyl-4-(2,2-diethoxyethyl)-4H-1,2,4-triazole-5-thione as crystals was collected by filtration. Recrystallization from aqueous ethanol yielded colorless crystals melting at 87°-88° C.

Elemental analysis, for $C_{15}H_{21}N_3O_2S$; Calcd. C, 58.60; H, 6.89; N, 13.67; Found C, 58.50; H, 6.93; N, 13.77.

REFERENCE EXAMPLE 3

In 3 ml of methanol was dissolved 0.307 g of the 3-benzyl-4-(2,2-diethoxyethyl)-4H-1,2,4-triazole-5-thione prepared in Reference Example 2, followed by addition of 0.6 ml of a 2N solution of sodium methoxide in methanol. Under stirring, 0.07 ml of methyl iodide was added dropwise and, after 30 minutes, the methanol was evaporated off. The residue was diluted with water and extracted with chloroform. The chloroform layer was washed with water, dried over $Na_2SO_4$. Evaporation of the solvent gave 3-benzyl-4-(2,2-diethoxyethyl)-5-methylthio-4H-1,2,4-triazole as an oil (quantitative yield).

NMR: $\delta(CDCl_3)$ 1.20(6H, t), 2.75(3H, s), 3.50(4H, d-q), 3.80(2H, d, J=5Hz), 4.30(2H, s), 4.40(1H, t, J=5Hz), 7.30(4H).

Elemental analysis, for $C_{16}H_{23}N_3O_2S$; Calcd. C, 59.78; H, 7.21; N, 13.07; Found C, 59.26; H, 7.15; N, 12.99.

REFERENCE EXAMPLE 4

By a procedure similar to that of Reference Example 3, from 3-benzyl-4-(2,2-diethoxyethyl)-4H-1,2,4-triazole-5-thione, was obtained 3-benzyl-4-(2,2-diethoxyethyl)-5-ethylthio-4H-1,2,4-triazole as an oil.

NMR: $\delta(CDCl_3)$ 1.20(6H, t, J=7Hz), 1.45(3H, t, J=8Hz), 3.10-3.80(6H, m), 3.80(2H, d, J=5Hz), 4.30(2H, s), 4.40(1H, t, J=5Hz), 7.25(4H, s).

REFERENCE EXAMPLE 5

To a solution of 1.9 g of aminoacetone ethylene acetal in 26 ml of tetrahydrofuran was added 1.7 ml of triethylamine with stirring, followed by the dropwise addition of 0.8 ml of carbon disulfide. After 10 minutes, 1.3 ml of ethyl chlorocarbonate was added dropwise and, at room temperature, the mixture was stirred for 20 minutes. The solvent was evaporated off and the residue extracted with chloroform. The chloroform layer was washed with water and dried over $Na_2SO_4$. The solvent was evaporated off and the oily residue was dissolved in 20 ml of benzene. Following the addition of 1.7 g of phenylacetic acid hydrazide, the solution was refluxed for 10 minutes. The solvent was then evaporated off. This procedure yielded 4-(2,2-ethylenedioxypropyl)-1-phenylacetylthiosemicarbazide

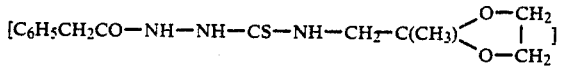

as an oil. To this oil was added 20 ml of a 2N-aqueous solution of potassium hydroxide and the mixture was heated on a water bath at 90° C. for 15 minutes. After cooling, 2.6 g of ammonium chloride was added and the precipitate was recovered by filtration. The resultant crystals of 1-(3-benzyl-1,5-dihydro-5-thioxo-4H-1,2,4-triazol-4-yl)-2-propanone ethylenacetal were recrystallized from aqueous methanol. Above procedure yielded colorless prisms melting at 119°-120° C.

Elemental analysis, for $C_{14}H_{17}N_3O_2S$; Calcd. C, 57.71; H, 5.88; N, 14.42; Found C, 57.82; H, 5.79; N, 14.50.

REFERENCE EXAMPLE 6

To 10 ml of ethanol was added 1.1 g of the 1-(3-benzyl-1,5-dihydro-5-thioxo-4H-1,2,4-triazol-4-yl)-2-propanone ethylenacetal obtained in Reference Example 5, followed by addition of 5.0 ml of 2N-hydrochloric acid. The mixture was refluxed for 40 minutes and, then, concentrated to half the original volume. To the concentrate was added water and the resultant precipitate was recovered by filtration. This procedure provided 1-(3-benzyl-1,5-dihydro-5-thioxo-4H-1,2,4-triazol-4-yl)-2-propanone as crystals. Recrystallization from ethyl acetate gave colorless needles melting at 163°-165° C.

Elemental analysis, for $C_{12}H_{13}N_3OS$; Calcd. C, 58.27; H, 5.30; N, 16.99; Found C, 58.51; H, 5.22; N, 17.13.

REFERENCE EXAMPLE 7

By a procedure similar to that of Reference Example 3, from 1-(3-benzyl-1,5-dihydro-5-thioxo-4H-1,2,4-triazol-4-yl)-2-propanone, was obtained 1-(3-benzyl-5-methylthio-4H-1,2,4-triazol-4-yl)-2-propanone as crystals. Recrystallization from ethyl acetate provided colorless prisms melting at 113°-114° C.

Elemental analysis, for $C_{13}H_{15}N_3OS$; Calcd. C, 59.74; H, 5.79; N, 16.08; Found C, 59.68; H, 5.72; N, 16.21.

REFERENCE EXAMPLE 8

As in Reference Example 1, from methylphenylacetic acid hydrazide, 4-(2,2-diethoxyethyl)-1-(α-methylphenylacetyl)thiosemicarbazide was obtained. Colorless prisms melting at 105°-106° C. (as recrystallized from aqueous methanol).

Elemental analysis, for $C_{16}H_{25}N_3O_3S$; Calcd. C, 56.61; H, 7.42; N, 12.38; Found C, 56.38; H, 7.40; N, 12.42.

REFERENCE EXAMPLE 9

By a procedure similar to that described in Reference Example 2, from 4-(2,2-diethoxyethyl)-1-(α-methylphenylacetyl)thiosemicarbazide, was obtained 4-(2,2-diethoxyethyl)-3-(α-methylbenzyl)-4H-1,2,4-triazole-5-thione as an oil.

REFERENCE EXAMPLE 10

By a procedure similar to that described in Reference Example 3, from 4-(2,2-diethoxyethyl)-3-(α-methylbenzyl)-4H-1,2,4-triazole-5-thione, was obtained 4-(2,2-diethoxyethyl)-3-(α-methylbenzyl)-5-methylthio-4H-1,2,4-triazole as an oil.

REFERENCE EXAMPLE 11

By a procedure similar to that described in Reference Example 1, from 4-chlorophenylacetic acid hydrazide, was obtained 1-(4-chlorophenylacetyl)-4-(2,2-diethoxyethyl)thiosemicarbazide as colorless needles melting at 107°-109° C. (as recrystallized from ethanol).

Elemental analysis, for $C_{15}H_{22}ClN_3O_3S$; Calcd. C, 50.06; H, 6.16; N, 11.68; Found C, 50.28; H, 6.14; N, 12.09.

REFERENCE EXAMPLE 12

By a procedure similar to that described in Reference Example 2, from 1-(4-chlorophenylacetyl)-4-(2,2-diethoxyethyl)thiosemicarbazide and 2N-sodium hydroxide, was obtained 3-(4-chlorobenzyl)-4-(2,2-diethoxyethyl)-4H-1,2,4-triazole-5-thione as colorless needles melting at 164°-165° C. (as recrystallized from methanol).

Elemental analysis, for $C_{15}H_{20}ClN_3O_2S$; Calcd. C, 52.70; H, 5.90; N, 12.29; Found C, 52.77; H, 5.97; N, 12.28.

REFERENCE EXAMPLE 13

By a procedure similar to that described in Reference Example 3, from 3-(4-chlorobenzyl)-4-(2,2-diethoxyethyl-4H-1,2,4-triazole-5-thione, was obtained 3-(4-chlorobenzyl)-4-(2,2-diethoxyethyl)-5-methylthio-4H-1,2,4-triazole as an oil.

REFERENCE EXAMPLE 14

By a procedure similar to that described in Reference Example 1, from diphenylacetic acid hydrazide, was obtained 1-diphenylacetyl-4-(2,2-diethoxyethyl)thiosemicarbazide as crystals. Recrystallization from ethanol yielded colorless needles melting at 151°-152° C.

Elemental analysis, for $C_{21}H_{27}N_3O_3S$; Calcd. C, 62.81; H, 6.78; N, 10.47; Found C, 63.07; H, 6.80; N, 10.54.

REFERENCE EXAMPLE 15

By a procedure similar to that described in Reference Example 2, from 1-diphenylacetyl-4-(2,2-diethoxyethyl)thiosemicarbazide, was obtained 4-(2,2-diethoxyethyl)-3-diphenylmethyl-4H-1,2,4-triazole-5-thione as crystals. Recrystallization from ethyl acetate-n-hexane yielded colorless needles melting at 155°-156° C.

Elemental analysis, for $C_{21}H_{25}N_3O_2S$; Calcd. C, 65.77; H, 6.57; N, 10.96; Found C, 65.82; H, 6.58; N, 10.93.

REFERENCE EXAMPLE 16

By a procedure described in Reference Example 3, from 4-(2,2-diethoxyethyl)-3-diphenylmethyl-4H-1,2,4-triazole-5-thione, was obtained 4-(2,2-diethoxyethyl)-3-diphenylmethyl-5-methylthio-4H-1,2,4-triazole as crystals. Recrystallization from acetone-n-hexane yielded colorless prisms melting at 80°-81° C.

Elemental analysis, for $C_{22}H_{27}N_3O_2S$; Calcd. C, 66.47; H, 6.85; N, 10.57; Found C, 66.76; H, 6.72; N, 10.44.

REFERENCE EXAMPLE 17

By a procedure similar to that of Reference Example 1, from 4-methylphenylacetic acid hydrazide, was obtained 4-(2,2-diethoxyethyl)-1-(4-methylphenylacetyl)thiosemicarbazide as crystals. Recrystallization from aqueous ethanol yielded colorless needles melting at 122°-123° C.

Elemental analysis, for $C_{16}H_{25}N_3O_3S$; Calcd. C, 56.61; H, 7.42; N, 12.38; Found C, 56.07; H, 7.38; N, 12.38.

REFERENCE EXAMPLE 18

By a procedure similar to that of Reference Example 2, from 4-(2,2-diethoxyethyl)-1-(4-methylphenylacetyl)thiosemicarbazide, was obtained 4-(2,2-diethoxyethyl)-3-(4-methylbenzyl)-4H-1,2,4-triazole-5-thione as crystals. Recrystallization from aqueous ethanol yielded colorless needles melting at 110°-111° C.

Elemental analysis, for $C_{16}H_{23}N_3O_2S$; Calcd. C, 59.78; H, 7.21; N, 13.07; Found C, 59.80; H, 7.14; N, 13.21.

REFERENCE EXAMPLE 19

By a procedure similar to that of Reference Example 3, from 4-(2,2-diethoxyethyl)-3-(4-methylbenzyl)-4H-1,2,4-triazole-5-thione, was obtained 4-(2,2-diethoxyethyl)-3-(4-methylbenzyl)-5-methylthio-4H-1,2,4-triazole as an oil.

NMR: $\delta(CDCl_3)$ 1.30(6H, t), 2.45(3H, s), 2.85(3H, s), 3.20-4.05(4H, m), 3.90(2H, d), 4.40 (2H, s), 4.45(1H, t), 7.25(4H, s)

REFERENCE EXAMPLE 20

By a procedure similar to that of Reference Example 1, from 4-methoxyphenylacetic acid hydrazide, was obtained 4-(2,2-diethoxyethyl)-1-(4-methoxyphenylacetyl)thiosemicarbazide as crystals. Recrystallization from ethanol yielded colorless needles melting at 120°-121° C.

Elemental analysis, for $C_{16}H_{25}N_3O_4S$; Calcd. C, 54.06; H, 7.09; N, 11.82; Found C, 53.80; H, 7.12; N, 11.62.

REFERENCE EXAMPLE 21

By a procedure similar to that of Reference Example 2, from 4-(2,2-diethoxyethyl)-1-(4-methoxyphenylacetyl)thiosemicarbazide, was obtained 4-(2,2-diethoxyethyl)-3-(4-methoxybenzyl)-4H-1,2,4-triazole-5-thione as crystals. Recrystallization from aqueous ethanol yielded colorless needles melting at 115°-116° C.

Elemental analysis, for $C_{16}H_{23}N_3O_3S$; Calcd. C, 56.95; H, 6.87; N, 12.45; Found C, 56.97; H, 6.82; N, 12.58.

REFERENCE EXAMPLE 22

By a procedure similar to that of Reference Example 3, from 4-(2,2-diethoxyethyl)-3-(4-methoxybenzyl)-4H-1,2,4-triazole-5-thione, was obtained 4-(2,2-diethoxyethyl)-3-(4-methoxybenzyl)-5-methylthio-4H-1,2,4-triazole as an oil.

NMR: $\delta(CDCl_3)$ 1.30(6H, t), 2.85(3H, s), 3.20–4.00(6H, m), 3.90(3H, s), 4.35(2H, s), 4.50(1H, t), 6.80–7.60(4H, m).

REFERENCE EXAMPLE 23

By a procedure similar to that of Reference Example 1, from 3-methoxyphenylacetic acid hydrazide, was obtained 4-(2,2-diethoxyethyl)-1-(3-methoxyphenylacetyl)thiosemicarbazide as crystals. Recrystallization from aqueous methanol yielded colorless needles melting at 109°-111° C.

Elemental analysis, for $C_{16}H_{25}N_3O_4S$; Calcd. C, 54.06; H, 7.09; N, 11.82; Found C, 53.74; H, 6.88; N, 12.07.

REFERENCE EXAMPLE 24

By a procedure similar to that of Reference Example 2, from 4-(2,2-diethoxyethyl)-1-(3-methoxyphenylacetyl)thiosemicarbazide, was obtained 4-(2,2-diethoxyethyl)-3-(3-methoxybenzyl)-4H-1,2,4-triazole-5-thione as crystals. Recrystallization from aqueous methanol yielded colorless needles melting at 67°-69° C.

Elemental analysis, for $C_{16}H_{23}N_3O_3S$; Calcd. C, 56.95; H, 6.87; N, 12.45; Found C, 56.64; H, 6.75; N, 12.46.

REFERENCE EXAMPLE 25

By a procedure similar to that of Reference Example 3, from the product of Reference Example 24, was obtained 4-(2,2-diethoxyethyl)-3-(3-methoxybenzyl)-5-methylthio-4H-1,2,4-triazole as an oil.

NMR: $\delta(CDCl_3)$ 1.20(6H, t), 2.75(3H, s), 3.20–3.80(4H, m), 3.75(3H, s), 3.75(2H, d), 4.30(2H, s), 4.35(1H, t), 6.70–7.40(4H, m).

REFERENCE EXAMPLE 26

To 2 ml of ethylene glycol was added 0.2 g of potassium hydroxide, followed by addition of 0.23 g of 3-methylthio-11H-s-triazolo[3,4-b][3]benzazepine. The mixture was stirred at 150°-160° C. for 2 hours, after which water was added. The mixture was made acidic with 4N-hydrochloric acid and extracted with chloroform. The chloroform layer was washed with water and dried over $Na_2SO_4$. The solvent was evaporated off and the residue was treated with ethyl acetate. By the above procedure was obtained 2,11-dihydro-3H-s-triazolo[3,4-b][3]benzazepin-3-one as crystals. Recrystallization from methanol yielded light-brown needles melting at 207°-208° C. The following compounds were produced by procedures similar to that of the above Reference Example.

11-Methyl-3-methylthio-11H-s-triazolo[3,4-b][3]benzazepine was treated with potassium hydroxide and the reaction mixture was treated as described. By this procedure was obtained 2,11-dihydro-11-methyl-3H-s-triazolo[3,4-b][3]benzazepin-3-one as crystals. Pale brown needles (as recrystallized from ethanol), m.p. 119°-120° C.

3-Methylthio-11-phenyl-11H-s-triazolo[3,4-b][3]benzazepine was treated with potassium hydroxide and the reaction mixture was treated as described. This procedure provided 2,11-dihydro-11-phenyl-3H-s-triazolo[3,4-b][3]benzazepin-3-one as crystals. Colorless needles (as recrystallized from methanol), m.p. 258°-260° C.

From 8-chloro-3-methylthio-11H-s-triazolo[3,4-b][3]benzazepine, was obtained 8-chloro-2,11-dihydro-3H-s-triazolo[3,4-b][3]benzazepin-3-one as crystals. Colorless platelets (as recrystallized from chloroform-methanol), m.p. 281°-283° C.

From 8-methyl-3-methylthio-11H-s-triazolo[3,4-b][3]benzazepine, was obtained 2,11-dihydro-8-methyl-3H-s-triazolo[3,4-b][3]benzazepin-3-one as crystals. Colorless platelets (as recrystallized from chloroform-methanol), m.p. 232°-234° C.

From 9-methoxy-3-methylthio-11H-s-triazolo[3,4-b][3]benzazepine, was obtained 2,11-dihydro-9-methoxy-3H-s-triazolo[3,4-b][3]benzazepin-3-one as crystals. Colorless needles (as recrystallized from chloroform-methanol), m.p. 271°-274° C.

REFERENCE EXAMPLE 27

To 2.3 g of 8-chloro-3-methylsulfonyl-11H-s-triazolo[3,4-b][3]benzazepine in 20 ml of dioxane was added 10 ml of 2N-potassium hydroxide and the mixture was heated on a water bath at 95° C. for 30 minutes. The solvent was evaporated off and water was added to the residue. The mixture was made acidic with 2N-HCl and the resultant crystalline precipitate was recovered by filtration and dried. By the above procedure was obtained 8-chloro-2,11-dihydro-3H-s-triazolo[3,4-b][3]benzazepin-3-one as crystals. Recrystallization from chloroform-methanol yielded colorless platelets, m.p. 281°-283° C.

Elemental analysis, for $C_{11}H_8ClN_3O$; Calcd. C, 56.54; H, 3.45; N, 17.99; Found C, 56.30; H, 3.25; N, 17.83.

REFERENCE EXAMPLE 28

By a procedure similar to that described in Reference Example 27, from 8-methyl-3-methylsulfonyl-11H-s-triazolo[3,4-b][3]benzazepine, was obtained 8-methyl-2,11-dihydro-3H-s-triazolo[3,4-b][3]benzazepin-3-one as crystals. Recrystallization from chloroform-methanol provided colorless platelets, m.p. 232°-234° C.

Elemental analysis, for $C_{12}H_{11}N_3O$; Calcd. C, 67.59; H, 5.20; N, 19.71; Found C, 67.31; H, 5.10; N, 19.80.

REFERENCE EXAMPLE 29

To 3 ml of 80% phosphoric acid was added 0.245 g of 3-methylsulfinyl-11H-s-triazolo[3,4-b][3]benzazepine and the mixture was heated on an oil bath at 130°-140° C. for 1 hour. Following addition of water, the crystals were collected by filtration and dried. By the above procedure was obtained 2,11-dihydro-3H-s-triazolo[3,4-b][3]benzazepin-3-one. Recrystallization from chloroform-methanol yielded colorless needles, m.p. 210°–211° C.

REFERENCE EXAMPLE 30

By a procedure similar to that described in Reference Example 29, from 8-methyl-3-methylsulfinyl-11H-s-triazolo[3,4-b][3]benzazepine, was obtained 2,11-dihydro-8-methyl-3H-s-triazolo[3,4-b][3]benzazepin-3-one as crystals. Recrystallization from chloroform-methanol yielded colorless platelets, m.p. 233°–234° C.

REFERENCE EXAMPLE 31

To 1.15 g of 3-methylthio-11H-s-triazolo[3,4-b][3]benzazepine in 20 ml of ethanol was added 6 ml of Raney nickel (wet) and the mixture was refluxed for 15 minutes under stirring. The Raney nickel was filtered off and the solvent was removed from the filtrate. To the residue was added water. By this procedure was obtained 11H-s-triazolo[3,4-b][3]benzazepine as crystals. Recrystallization from ethanol-n-hexane yielded colorless needles, m.p. 157°–158° C. The infrared absorption spectrum was identical with the spectrum of the same compound obtained by reacting 2-hydrazino-3-benzazepine with ortho-formic acid ester.

The following compound was produced by a procedure similar to that described in the above Reference Example.

3-Methylthio-11-phenyl-11H-s-triazolo[3,4-b][3]benzazepine was treated with Raney nickel as described. This procedure provided 11-phenyl-11H-s-triazolo[3,4-b][3]benzazepine as crystals. Colorless prisms (as recrystallized from ethanol), m.p. 217°–218° C.

REFERENCE EXAMPLE 32

To 1.83 g of 11H-s-triazolo[3,4-b][3]benzazepine in 40 ml of chloroform was added 0.1 ml of pyridine and 0.55 ml of bromine was added dropwise under stirring. The mixture was stirred for 2 hours, after which it was washed with water and dried over $Na_2SO_4$. After evaporation of the solvent, the residue was treated with ether. By the above procedure was obtained 3-bromo-11H-s-triazolo[3,4-b][3]benzazepine as crystals. These crystals were recrystallized from ethanol and methanol in the order mentioned to obtain pale-brown platelets melting at 169°–170° C.

Elemental analysis, for $C_{11}H_8BrN_3$; Calcd. C, 50.40; H, 3.08; N, 16.03; Found C, 50.87; H, 3.12; N, 15.78.

EXAMPLE 1

To a solution of 6.15 g of 3-benzyl-4-(2,2-diethoxyethyl)-4H-1,2,4-triazolo-5-thione in 36 ml of methanol was added 12 ml of 2 N sodium methoxide/methanol followed by the addition of 1.48 ml of methyl iodide with stirring. The reaction mixture was then treated as described in Reference Example 3 to obtain 3-benzyl-4-(2,2-diethoxyethyl)-5-methylthio-1,2,4-triazole as an oil (nearly quantitative yield). To the entire amount of this oily product was added 40 ml of a 70% aqueous solution of perchloric acid and the mixture was heated at 80°–90° C. After 25 minutes, ice-water was added to the mixture, whereupon an oil separated. The supernatant fluid was removed by decantation and the residue was neutralized by the addition of a saturated aqueous solution of sodium hydrogen carbonate and extracted with chloroform. The chloroform layer was washed with water and dried over $Na_2SO_4$. The solvent was evaporated off and the residue was treated with ethyl acetate. The resultant crystals of 3-methylthio-11H-s-triazolo[3,4-b][3]benzazepine were recrystallized from methanol. The above procedure yielded colorless needles melting at 168°–169° C.

Elemental analysis, for $C_{12}H_{11}N_3S$; Calcd. C, 62.85; H, 4.84; N, 18.33; Found C, 62.86; H, 4.70; N, 18.61.

EXAMPLE 2

In 1 l of methanol was dissolved 11.0 g of sodium, followed by the addition of 134.4 g of 3-benzyl-4-(2,2-diethoxyethyl)-4H-1,2,4-triazole-5-thione. Then, 30.0 ml of methyl iodide was added dropwise and the mixture was stirred for 20 minutes. Thereafter, the reaction mixture was treated as in Reference Example 3 to obtain 140 g of 3-benzyl-4-(2,2-diethoxyethyl)-5-methylthio-1,2,4-triazole as an oil. This oil was gradually added to 430 ml of concentrated sulfuric acid previously cooled with ice-sodium chloride and, then at room temperature, the mixture was stirred for 30 minutes, after which it was poured into 5 l of ice-water. The mixture was neutralized with concentrated aqueous ammonia and the resultant crystals were collected by filtration. The crystalline 3-methylthio-11H-s-triazolo[3,4-b][3]benzazepine thus obtained was recrystallized from methanol. This procedure yielded colorless needles melting at 168°–169° C. Infrared absorption spectrum of this product was identical with that of the product obtained in Example 1.

EXAMPLE 3

To 10 ml of concentrated sulfuric acid, previously cooled with ice-sodium chloride, was added 3.2 g of the 3-benzyl-4-(2,2-diethoxyethyl)-5-ethylthio-4H-1,2,4-triazole prepared in Reference Example 4. The mixture was allowed to stand at room temperature for 15 minutes, after which it was treated as in Example 2. The resultant 3-ethylthio-11H-s-triazolo[3,4-b][3]benzazepine was recrystallized from ethyl acetate. This procedure yielded colorless prisms melting at 94°–95° C.

Elemental analysis, for $C_{13}H_{13}N_3S$; Calcd. C, 64.17; H, 5.39; N, 17.27; Found C, 64.09; H, 5.29; N, 17.40.

EXAMPLE 4

To 0.3 g of the 1-(3-benzyl-5-methylthio-4H-1,2,4-triazol-4-yl)-2-propanone obtained in Reference Example 7 was added 15.0 g of polyphosphoric acid and the mixture was heated on an oil bath at 160°–170° C. for 4 hours. The reaction mixture was poured into ice-water, neutralized with concentrated aqueous ammonia and extracted with chloroform. The chloroform layer was washed with water and dried over $Na_2SO_4$. The solvent was evaporated off and the residue was treated with isopropyl ether. By the above procedure, 6-methyl-3-methylthio-11H-s-triazolo[3,4-b][3]benzazepine was obtained as crystals. Recrystallization from ethyl acetate gave colorless platelets melting at 129°–130° C.

Elemental analysis, for $C_{13}H_{13}N_3S$; Calcd. C, 64.17; H, 5.39; N, 17.27; Found C, 64.09; H, 5.27; N, 17.25.

EXAMPLE 5

12.5 g of the 4-(2,2-diethoxyethyl)-3-(α-methylbenzyl)-5-methylthio-4H-1,2,4-triazole prepared in Reference Example 10 was added to cold concentrated sulfuric acid and the cyclization reaction mixture was treated by a procedure similar to that described in Example 2. By the above procedure was obtained 11-methyl-3-methylthio-11H-s-triazolo[3,4-b][3]benzazepine as an oil.

NMR: δ(CDCl₃) 1.70(3H, d), 2.80(3H, s), 4.45(1H, q), 6.75(2H, d-d), 7.40(4H).

EXAMPLE 6

To the entire amount of 3-(4-chlorobenzyl)-4-(2,2-diethoxyethyl)-5-methylthio-4H-1,2,4-triazole as produced from 1.7 g of 3-(4-chlorobenzyl)-4-(2,2-diethoxyethyl)-4H-1,2,4-triazole-5-thione in Reference Example 13, there was added 10 ml of a 70% aqueous solution of perchloric acid and the cyclization reaction was carried out at 90°-95° C. for 1¾ hours as described in Example 1. The reaction mixture was further treated as in Example 1 to obtain 8-chloro-3-methylthio-11H-s-triazolo[3,4-b][3]benzazepine as crystals. Recrystallization from methanol yielded colorless needles melting at 166°-167° C.

Elemental analysis, for C₁₂H₁₀ClN₃S; Calcd. C, 54.64; H, 3.82; N, 15.93; Found C, 54.62; H, 3.71; N, 16.18.

EXAMPLE 7

By a procedure similar to that described in Example 1, 20.0 g of the 4-(2,2-diethoxyethyl)-3-diphenylmethyl-5-methylthio-4H-1,2,4-triazole prepared in Reference Example 16 was added to 50 ml of a 70% aqueous solution of perchloric acid under ice-cooling and the mixture was heated at 60°-65° C. for 20 minutes. The cyclization reaction mixture was further treated as described to obtain 3-methylthio-11-phenyl-11H-s-triazolo[3,4-b][3]benzazepine as crystals. Recrystallization from ethanol yielded colorless platelets melting at 169°-170° C.

Elemental analysis, for C₁₈H₁₅N₃S; Calcd. C, 70.79; H, 4.95; N, 13.76; Found C, 71.10; H, 4.89; N, 14.05.

EXAMPLE 8

To 3 ml of methanol was added 0.215 g of 2,11-dihydro-3H-s-triazolo[3,4-b][3]benzazepine-3-thione and, under stirring, 0.6 ml of 2N-sodium methoxide/methanol was added. Then, 0.07 ml of methyl iodide was added dropwise. After 20 minutes, the reaction mixture was extracted with ethyl acetate. The ethyl acetate layer was washed with water and dried over Na₂SO₄. The solvent was then evaporated off and the residue was treated with ether. In this manner, 3-methylthio-11H-s-triazolo[3,4-b][3]benzazepine were obtained as crystals. Recrystallization from methanol yielded colorless needles melting at 168°-169° C. This was identical with the products obtained in Examples 1 and 2.

The following compound was produced by a procedure similar to that of the above example.

The reaction of 2,11-dihydro-3H-s-triazolo[3,4-b][3]benzazepine-3-thione with benzyl bromide in the presence of sodium methoxide gave 3-benzylthio-11H-s-triazolo[3,4-b][3]benzazepine.

NMR: δ(CDCl₃) 4.05(2H, s), 4.35(2H, s), 6.55(2H, d-d), 7.05-7.55(9H, m)

EXAMPLE 9

By a procedure similar to that of Reference Example 3, from 3-(4-chlorobenzyl)-4-(2,2-diethoxyethyl)-4H-1,2,4-triazole-5-thione, was obtained 3-(4-chlorobenzyl)-4-(2,2-diethoxyethyl)-5-methylthio-4H-1,2,4-triazole as an oil. This oil was added to 75 ml of concentrated sulfuric acid and the mixture was after-treated as described in Example 2. By this procedure was obtained 8-chloro-3-methylthio-11H-s-triazolo[3,4-b][3]benzazepine as crystals. Recrystallization from methanol yielded colorless needles melting at 167°-168° C. Infrared absorption spectrum was identical with that of the product obtained in Example 6.

EXAMPLE 10

By a procedure similar to that of Example 2, from 4-(2,2-diethoxyethyl)-3-(4-methylbenzyl)-5-methylthio-4H-1,2,4-triazole obtained in Reference Example 19, was obtained 8-methyl-3-methylthio-11H-s-triazolo[3,4-b][3]benzazepine as crystals. Recrystallization from ethyl acetate yielded colorless needles melting at 161°-162° C.

Elemental analysis, for C₁₃H₁₃N₃S; Calcd. C, 64.17; H, 5.39; N, 17.27; Found C, 63.92; H, 5.33; N, 17.32.

EXAMPLE 11

By a procedure similar to that of Example 4, from 4-(2,2-diethoxyethyl)-3-(4-methoxybenzyl)-5-methylthio-4H-1,2,4-triazole obtained in Reference Example 22, was obtained 8-methoxy-3-methylthio-11H-s-triazolo[3,4-b][3]benzazepine as crystals. Recrystallization from ethyl acetate yielded colorless needles melting at 167°-168° C.

Elemental analysis, for C₁₃H₁₃N₃OS; Calcd. C, 60.21; H, 5.05; N, 16.21; Found C, 60.08; H, 4.91; N, 15.87.

EXAMPLE 12

By a procedure similar to that of Example 4, from 4-(2,2-diethoxyethyl)-3-(3-methoxybenzyl)-5-methylthio-4H-1,2,4-triazole obtained in Reference Example 25, was obtained 9-methoxy-3-methylthio-11H-s-triazolo[3,4-b][3]benzazepine as crystals. Recrystallization from ethyl acetate yielded colorless prisms melting at 138°-139° C.

Elemental analysis, for C₁₃H₁₃N₃OS; Calcd. C, 60.21; H, 5.05; N, 16.21; Found C, 60.09; H, 5.01; N, 16.26.

EXAMPLE 13

To 100 ml of dioxane were added 4.6 g of 3-methylthio-11H-s-triazolo[3,4-b][3]benzazepine and 6.7 g of selenium dioxide. The mixture was refluxed for 7.5 hours under stirring. The insolubles were filtered off when hot and the filtrate was concentrated. The resultant crystals were recovered by filtration, washed with ethanol and dried, whereupon 3-methylthio-11H-s-triazolo[3,4-b][3]benzazepin-11-one was obtained as crystals. Recrystallization from methanol yielded pale-yellow platelets melting at 162°-163° C.

Elemental analysis, for C₁₂H₉N₃OS; Calcd. C, 59.24; H, 3.72; N, 17.27; Found C, 59.20; H, 3.61; N, 17.17.

EXAMPLE 14

By a procedure similar to that described in Example 13, the reaction of 8-chloro-5-methylthio-11H-s-triazolo[3,4-b][3]benzazepine with selenium dioxide gave 8-chloro-3-methylthio-11H-s-triazolo[3,4-b][3]benzazepin-11-one as crystals. Recrystallization from chloroform-methanol yielded colorless platelets melting at 254°-255° C.

Elemental analysis, for C₁₂H₈ClN₃OS; Calcd. C, 51.89; H, 2.90; N, 15.13; Found C, 51.79; H, 2.78; N, 15.06.

EXAMPLE 15

By a procedure similar to that described in Examples 13, the reaction of 8-methyl-3-methylthio-11H-s-triazolo[3,4-b][3]benzazepine with selenium dioxide gave 8-methyl-3-methylthio-11H-s-triazolo[3,4- b][3]benzazepin-11-one as crystals. Recrystallization from methanol yielded colorless platelets melting at 178°–179° C.

Elemental analysis, for $C_{13}H_{11}N_3OS$; Calcd. C, 60.68; H, 4.31; N, 16.33; Found C, 60.53; H, 4.49; N, 16.30.

EXAMPLE 16

To 4.6 g of 3-methylthio-11H-s-triazolo[3,4-b][3]benzazepine in 60 ml of tetrahydrofuran was added 2.4 g of paraformaldehyde together with 4.0 ml of a 40% solution of trimethylbenzylammonium hydroxide in methanol. After refluxing the mixture for 30 minutes, the solvent was evaporated off. The residue was diluted with water and extracted with ethyl acetate. The ethyl acetate layer was washed with water and dried over $Na_2SO_4$. The solvent was then evaporated off and the residual crystals were collected by filtration, washed with isopropyl alcohol and dried. The above procedure provided 11-methylene-3-methylthio-11H-s-triazolo[3,4-b][3]benzazepine as crystals. Recrystallization from ethyl acetate yielded colorless needles melting at 121°–122° C.

Elemental analysis, for $C_{13}H_{11}N_3S$; Calcd. C, 64.70; H, 4.59; N, 17.42; Found C, 64.79; H, 4.52; N, 17.34.

EXAMPLE 17

A solution of 4.6 g of 3-methylthio-11H-s-triazolo[3,4-b][3]benzazepine in 100 ml of dichloromethane was stirred under ice-cooling and 5.2 g of m-chloroperbenzoic acid was added. The mixture was further stirred for 40 minutes, after which it was washed with a solution of sodium sulfite, a saturated solution of sodium hydrogen carbonate and water in the order mentioned, and followed by drying over $Na_2SO_4$. The solvent was then evaporated off and the crystalline residue was collected by filtration and washed with ethyl ether. The above procedure provided 3-methylsulfinyl-11H-s-triazolo[3,4-b][3]benzazepine as crystals. Recrystallization from methanol yielded colorless needles melting at 176°–177° C.

Elemental analysis, for $C_{12}H_{11}N_3OS$; Calcd. C, 58.75; H, 4.52; N, 17.13; Found C, 58.66; H, 4.40; N, 16.91.

EXAMPLE 18

By a procedure similar to that described in Example 17, 8-methyl-3-methylthio-11H-s-triazolo[3,4-b][3]benzazepine was reacted with m-chloroperbenzoic acid to obtain 8-methyl-3-methylsulfinyl-11H-s-triazolo[3,4-b][3]benzazepine. Colorless needles (as recrystallized from methanol), m.p. 158°–159° C.

Elemental analysis, for $C_{13}H_{13}N_3OS$; Calcd. C, 60.21; H, 5.05; N, 16.21; Found C, 60.24; H, 4.96; N, 15.88.

EXAMPLE 19

By a procedure similar to that described in Example 17, 8-chloro-3-methylthio-11H-s-triazolo[3,4-b][3]benzazepine was reacted with m-chloroperbenzoic acid to obtain 8-chloro-3-methylsulfinyl-11H-s-triazolo[3,4-b][3]benzazepine. Colorless needles (as recrystallized from methanol), m.p. 183°–185° C.

Elemental analysis, for $C_{12}H_{10}ClN_3OS$; Calcd. C, 51.52; H, 3.60; N, 15.02; Found C, 51.41; H, 3.43; N, 15.19.

EXAMPLE 20

By a procedure similar to that described in Example 17, 8-methoxy-3-methylthio-11H-s-triazolo[3,4-b][3]benzazepine was reacted with m-chloroperbenzoic acid to obtain 8-methoxy-3-methylsulfinyl-11H-s-triazolo[3,4-b][3]benzazepine. Colorless needles (as recrystallized from chloroform-methanol), m.p. 241°–242° C.

Elemental analysis, for $C_{13}H_{13}N_3O_2S$; Calcd. C, 56.71; H, 4.76; N, 15.26; Found C, 56.51; H, 4.71; N, 15.31.

EXAMPLE 21

By a procedure similar to that described in Example 17, 9-methoxy-3-methylthio-11H-s-triazolo[3,4-b][3]benzazepine was reacted with m-chloroperbenzoic acid to obtain 9-methoxy-3-methylsulfinyl-11H-s-triazolo[3,4-b][3]benzazepine. Colorless needles (as recrystallized from methanol), m.p. 176°–177° C.

Elemental analysis, for $C_{13}H_{13}N_3O_2S$; Calcd. C, 56.71; H, 4.76; N, 15.26 Found C, 56.37; H, 4.62; N, 15.17.

EXAMPLE 22

By a procedure similar to that described in Example 17, 3-ethylthio-11H-s-triazolo[3,4-b][3]benzazepine was reacted with m-chloroperbenzoic acid to obtain 3-ethylsulfinyl-11H-s-triazolo[3,4-b][3]benzazepine. Colorless needles (as recrystallized from ethyl acetate), m.p. 98°–99° C.

Elemental analysis, for $C_{13}H_{13}N_3OS$; Calcd. C, 60.21; H, 5.05; N, 16.21 Found C, 59.92; H, 4.98; N, 16.17.

EXAMPLE 23

Under ice-cooling, 0,.515 g of m-chloroperbenzoic acid was added to 0.23 g of 3-methylthio-11H-s-triazolo[3,4-b][3]benzazepine in 5 ml of dichloromethane and, after 5 minutes, the ice bath was removed. It was then allowed to stand at room temperature overnight. The reaction mixture was washed with a solution of sodium sulfite, an aqueous solution of sodium hydrogen carbonate and water in the order mentioned, followed by drying over $Na_2SO_4$. The solvent was evaporated off and the residue was treated with ethanol. The above procedure provided 3-methylsulfonyl-11H-s-triazolo[3,4-b][3]benzazepine as crystals. Recrystallization from ethanol yielded colorless needles melting at 110°–111° C.

Elemental analysis, for $C_{12}H_{11}N_3O_2S$; Calcd. C, 55.16; H, 4.24; N, 16.08; Found C, 54.88; H, 4.16; N, 16.06.

EXAMPLE 24

To a solution of 0.23 g of 3-methylthio-11H-s-triazolo[3,4-b][3]benzazepine in 2 ml of acetic acid was added 0.2 ml of concentrated sulfuric acid and 0.5 ml of 30% hydrogen peroxide was added dropwise under stirring. After 20 hours, a solution of sodium sulfite was added and the solvent was evaporated off. To the residue was added a saturated aqueous solution of sodium hydrogen carbonate and the mixture was extracted with chloroform. The chloroform layer was washed with water and dried over $Na_2SO_4$. The solvent was then evaporated off and the residue was treated with ethanol. By the above procedure was obtained 3-methylsulfonyl-11H-s-triazolo[3,4-b][3]benzazapine as crystals. m.p. 110°–111° C. Based on its infrared absorption spectrum and other data, this compound was identified with the compound obtained in Example 23.

EXAMPLE 25

To a solution of 6.1 g of 8-methyl-3-methylthio-11H-s-triazolo[3,4-b][3]benzazepine in 75 ml of acetic acid was added 5.0 ml of concentrated sulfuric acid and under ice-cooling and stirring, 12.5 ml of 30% $H_2O_2$ was added dropwise. After stirring the mixture for 10 minutes at room temperature, it was heated on a water bath at 60°–65° C. for 2 hours. After ice-cooling, an aqueous solution of sodium sulfite was added to decompose the excess hydrogen peroxide. The solvent was evaporated off and, following addition of water, the residue was neutralized with concentrated aqueous ammonia, again under ice-cooling, and extracted with chloroform. The chloroform layer was washed with water and dried over $Na_2SO_4$. The solvent was evaporated off and the residue was treated with ether. By the above procedure was obtained 8-methyl-3-methylsulfonyl-11H-s-triazolo[3,4-b][3]benzazepine as crystals. Recrystallization from ethanol yielded colorless needles melting at 152°–153° C.

Elemental aanlysis, for $C_{13}H_{13}N_3O_2S$; Calcd. C, 56.71; H, 4.76; N, 15.26; Found C, 56.67; H, 4.71; N, 15.42.

EXAMPLE 26

By a procedure similar to that of Example 25, oxidation of 8-chloro-3-methylthio-11H-s-triazolo[3,4-b][3]benzazepine, with aqueous 30% $H_2O_2$ solution gave 8-chloro-3-methylsulfonyl-11H-s-triazolo[3,4-b][3]benzazepine as a crystalline product. Recrystallization from chloroform-methanol yielded colorless prisms melting at 222°–223° C.

Elemental analysis, for $C_{12}H_{10}ClN_3O_2S$; Calcd. C, 48.73; H, 3.41; N, 14.21; Found C, 48.61; H, 3.37; N, 14.21.

EXAMPLE 27

By a procedure analogous to that described in Example 25, 8-methoxy-3-methylthio-11H-s-triazolo[3,4-b][3]benzazepine was reacted with a 30% aqueous solution of hydrogen peroxide to obtain 8-methoxy-3-methylsulfonyl-11H-s-triazolo[3,4-b][3]benzazepine as crystals. Recrystallization from methanol yielded colorless prisms melting at 145°–146° C.

Elemental analysis, for $C_{13}H_{13}N_3O_3S$; Calcd. C, 53.59; H, 4.50; N, 14.42; Found C, 53.61; H, 4.41; N, 14.59.

EXAMPLE 28

By a procedure similar to that described in Example 25, 9-methoxy-3-methylthio-11H-s-triazolo[3,4-b][3]benzazepine was reacted with 30% hydrogen peroxide to obtain 9-methoxy-3-methylsulfonyl-11H-s-triazolo[3,4-b][3]benzazepine as crystals. Recrystallization from ethyl acetate yielded colorless prisms melting at 146°–147° C.

Elemental analysis, for $C_{13}H_{13}N_3O_2S$; Calcd. C, 53.59; H, 4.50; N, 14.42; Found C, 53.42; H, 4.41; N, 14.42.

EXAMPLE 29

By a procedure similar to that of Example 24, the reaction of 3-methylthio-11-phenyl-11H-s-triazolo[3,4-b][3]benzazepine, with aqueous 30% $H_2O_2$ solution gave 3-methylsulfonyl-11-phenyl-11H-s-triazolo[3,4-b][3]benzazepine as crystals. Recrystallization from methanol yielded colorless needles, m.p. 175°–176° C.

Elemental analysis, for $C_{18}H_{15}N_3O_2S$; Calcd. C, 64.07; H, 4.48; N, 12.46; Found C, 63.93; H, 4.47; N, 12.58.

EXAMPLE 30

By a procedure similar to that of Example 24, the reaction of 11-methyl-3-methylthio-11H-s-triazolo[3,4-b][3]benzazepine, with aqueous 30% $H_2O_2$ solution gave 11-methyl-3-methylsulfonyl-11H-s-triazolo[3,4-b][3]benzazepine as crystals. Recrystallization from ethanol yielded colorless prisms, m.p. 147°–148° C.

Elemental analysis, for $C_{13}H_{13}N_3O_2S$; Calcd. C, 56.71; H, 4.76; N, 15.26; Found C, 56.49; H, 4.61; N, 15.22.

EXAMPLE 31

Under ice-cooling and stirring, 0.224 g of m-chloroperbenzoic acid was added to a solution of 0.243 g of 3-methylthio-11H-s-triazolo[3,4-b][3]benzazepine in 4 ml of dichloromethane. The mixture was stirred for 30 minutes, after which 0.035 g of m-chloroperbenzoic acid was further added. After additional stirring for 1 hour, the reaction mixture was shaken well with an aqueous solution of sodium sulfite and a saturated aqueous solution of sodium hydrogen carbonate. The dichloromethane layer was washed with water and dried over $Na_2SO_4$. The solvent was evaporated off and the crystalline precipitate was recovered by filtration and washed with ethyl acetate. The above procedure gave 3-methylsulfinyl-11H-s-triazolo[3,4-b][3]benzazepin-11-one as crystals. Recrystallization from chloroform-methanol yielded colorless needles, m.p. 208°–211° C.

Elemental analysis, for $C_{12}H_9N_3O_2S$; Calcd. C, 55.58; H, 3.50; N, 16.21; Found C, 55.82; H, 3.34; N, 16.17.

EXAMPLE 32

By a procedure similar to that of Example 17, the reaction of 11-methylene-3-methylthio-11H-s-triazolo[3,4-b][3]benzazepine with m-chloroperbenzoic acid gave 11-methylene-3-methylsulfinyl-11H-s-triazolo[3,4-b][3]benzazepine as crystals. Recrystallization from ethyl acetate yielded colorless prisms, m.p. 140°–142° C.

Elemental analysis, for $C_{13}H_{11}N_3OS$; Calcd. C, 60.68; H, 4.31; N, 16.33; Found C, 60.79; H, 4.27; N, 16.26.

EXAMPLE 33

To 0.230 g of 3-methylthio-11H-s-triazolo[3,4-b][3]benzazepine in 3 ml of acetic acid was added 0.2 ml of concentrated sulfuric acid and, under ice-cooling, 0.3 ml of a 30% aqueous solution of hydrogen peroxide was added dropwise. The mixture was allowed to stand at 3°–5° C. for 7 hours, at the end of which time an aqueous solution of sodium sulfite was added to the mixture to decompose the excess hydrogen peroxide. The solvent was evaporated off and the residue was diluted with water. The crystals were collected by filtration. By the above procedure was obtained 3-methylsulfinyl-11H-s-triazolo[3,4-b][3]benzazepine as crystals. Recrystallization from methanol yielded colorless needles, m.p. 176°–177° C. Based on infrared absorption spectrum and other data, this compound was identified with the compound obtained in Example 17.

EXAMPLE 34

To 0.522 g of 3-methylsulfonyl-11H-s-triazolo[3,4-b][3]benzazepine in 5 ml of methanol was added 3 ml of 2 N-sodium methoxide/methanol. The mixture was refluxed for 15 minutes and then the solvent was evaporated off. The residue was diluted with water and extracted with chloroform. The chloroform layer was washed with water and dried over $Na_2SO_4$. The solvent was then evaporated off and the residue was treated with isopropyl ether. By the above procedure was obtained 3-methoxy-11H-s-triazolo[3,4-b][3]benzazepine as crystals. Recrystallization from ethyl acetate-n-hexane yielded colorless prisms, melting point: 160°–161° C.

Elemental analysis, for $C_{12}H_{11}N_3O$; Calcd. C, 67.59; H, 5.20; N, 19.71; Found C, 67.31; H, 5.15; N, 19.72.

EXAMPLE 35

By a procedure similar to that described in Example 34, 3-methylsulfonyl-11H-s-triazolo[3,4-b][3] benzazepine was reacted with sodium ethoxide/ethanol, in lieu of sodium methoxide/methanol, to obtain 3-ethoxy-11H-s-triazolo[3,4-b][3]benzazepine as crystals. Recrystallization from acetone yielded colorless needles, melting point: 143°–144° C.

Elemental analysis, for $C_{13}H_{13}N_3O$; Calcd. C, 68.70; H, 5.77; N, 18.49; Found C, 68.47; H, 5.68; N, 18.33.

EXAMPLE 36

By a procedure similar to that described in Example 35, 0.245 g of 3-methylsulfinyl-11H-s-triazolo [3,4-b][3]benzazepine, in lieu of 3-methylsulfonyl-11H-s-triazolo[3,4-b][3]benzazepine, was reacted with 1.2 ml of 1 N-sodium ethoxide/ethanol in 2 ml of ethanol to obtain 3-ethoxy-11H-s-triazolo[3,4-b][3]benzazepine as crystals. Recrystallization from acetone yielded colorless needles, melting point 143°–144° C. The infrared absorption spectrum of this product was identical with that of the compound obtained in Example 35.

EXAMPLE 37

To a solution of 0.262 g of 3-bromo-11H-s-triazolo [3,4-b][3]benzazepine in 2 ml of methanol was added 1.0 ml of 2 N-sodium methoxide/methanol and the mixture was refluxed for one hour. The solvent was evaporated off and, following the addition of water, the residue was extracted with ethyl acetate. The ethyl acetate layer was washed with water and dried over $Na_2SO_4$. The solvent was then evaporated off and the residue was treated with isopropyl ether. By the above procedure was obtained 3-methoxy-11H-s-triazolo[3,4-b][3]benzazepine as crystals. Recrystallization from ethyl acetate-n-hexane yielded colorless prisms, melting point: 161°–162° C. The infrared absorption spectrum of this product was identical with that of the compound obtained in Example 34.

EXAMPLE 38

By procedures similar or analogous to the procedures described in the above Examples, the following compounds were obtained from the corresponding starting compounds.

The reaction of 8-methyl-3-methylsulfonyl-11H-s-triazolo[3,4-b][3]benzazepine with sodium methoxide yielded 3-methoxy-8-methyl-11H-s-triazolo[3,4-b][3]benzazepine. Colorless prisms (as recrystallized from ethyl acetate), melting point: 148°–149° C.

The reaction of 8-chloro-3-methylsulfonyl-11H-s-triazolo[3,4-b][3]benzazepine with sodium methoxide yielded 8-chloro-3-methoxy-11H-s-triazolo[3,4-b][3]benzazepine. Colorless needles (as recrystallized from aqueous acetone), melting point: 177°–178° C.

The reaction of 8-methoxy-3-methylsulfonyl-11H-s-triazolo[3,4-b][3]benzazepine with sodium methoxide yielded 3,8-dimethoxy-11H-s-triazolo[3,4-b][3]benzazepine. Colorless needles (as recrystallized from aqueous methanol), melting point: 185°–186° C.

The reaction of 9-methoxy-3-methylsulfonyl-11H-s-triazolo[3,4-b][3]benzazepine with sodium methoxide yielded 3,9-dimethoxy-11H-s-triazolo[3,4-b][3]benzazepine. Colorless needles (as recrystallized from aqueous acetone), melting point: 176°–177° C.

The reaction of 3-methylsulfonyl-11-phenyl-11H-s-triazolo[3,4-b][3]benzazepine with sodium methoxide yielded 3-methoxy-11-phenyl-11H-s-triazolo[3,4-b][3]benzazepine. Colorless prisms (as recrystallized from aqueous methanol), melting point: 183°–184° C.

The reaction of 11-methyl-3-methylsulfonyl-11H-s-triazolo[3,4-b][3]benzazepine with sodium methoxide yielded 3-methoxy-11-methyl-11H-s-triazolo[3,4-b][3]benzazepine. Colorless prisms (as recrystallized from ether), melting point: 101°–102° C.

The reaction of 3-bromo-11H-s-triazolo[3,4-b][3]benzazepine with sodium ethoxide yielded 3-ethoxy-11H-s-triazolo[3,4-b][3]benzazepine. Colorless needles (as recrystallized from acetone), melting point: 143°–144° C. Infrared absorption spectrum of this compound was identical with that of the products obtained in Examples 35 and 36.

The reaction of 11-methylene-3-methylsulfinyl-11H-s-triazolo[3,4-b][3]benzazepine with sodium methoxide yielded 3-methoxy-11-methylene-11H-s-triazolo[3,4-b][3]benzazepine. Colorless needles (as recrystallized from ethyl acetate), melting point: 160°–161° C.

The reaction of 3-methylsulfinyl-11H-s-triazolo [3,4-b][3]benzazepin-11-one with sodium methoxide yielded 3-methoxy-11H-s-triazolo[3,4-b][3]benzazepin-11-one. Colorless platelets (as recrystallized from methanol), melting point: 149°–150° C.

EXAMPLE 39

Manufacture of tablets for use as analgesics [Formula]

| | |
|---|---:|
| (1) 3-methylthio-11H-s-triazolo[3,4-b][3]benzazepine | 10 mg |
| (2) Lactose | 55 mg |
| (3) Corn starch | 34.5 mg |
| (4) Magnesium stearate | 0.5 mg |
| | 100 mg per tablet |

[Preparation]

After 22.5 mg of corn starch is admixed with (1) and (2), the mixture is granulated with a paste prepared from 7 mg of corn starch. To this granular mixture is added (4) together with 5 mg of corn starch and the entire composition is compression-molded into tablets measuring 7 mm in diameter.

What we claim is:

1. A compound of the formula

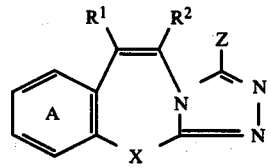

wherein $R^1$ and $R^2$ are hydrogen or alkyl having 1 to 4 carbon atoms, X is

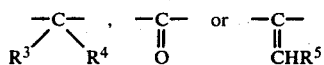

wherein $R^3$ and $R^4$ are hydrogen, alkyl having 1 to 4 carbon atoms, phenyl, or phenyl-$C_{1-4}$ alkyl, and $R^5$ is hydrogen or alkyl having 1 to 4 carbon atoms, Z is $-SR^6$, $-S(O)nR^6$ or $-OR^7$ wherein $R^6$ and $R^7$ are alkyl having 1–4 carbon atoms or phenyl-$C_{1-4}$ alkyl, and n is 1 or 2, and Ring A is unsubstituted or substituted with from one to four of halogen, lower alkyl, lower alkoxy and trifluoromethyl, or its physiologically acceptable salts.

2. The compound according to claim 1, wherein X is

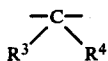

wherein $R^3$ and $R^4$ are defined as above, and Z is $-SR^6$ wherein $R^6$ is defined as above.

3. The compound according to claim 2, wherein $R^6$ is alkyl having 1 to 4 carbon atoms.

4. The compound according to claim 2, wherein $R^6$ is phenyl-$C_{1-4}$ alkyl.

5. The compound according to claim 1, wherein Z is $-S(O)nR^6$ (wherein $R^6$ and n are defined as above).

6. The compound according to claim 5, wherein $R^6$ is alkyl having 1 to 4 carbon atoms.

7. The compound according to claim 5, wherein $R^6$ is phenyl-$C_{1-4}$ alkyl.

8. The compound according to claim 1, wherein Z is $-OR^7$ wherein $R^7$ is defined as above.

9. The compound according to claim 8, wherein $R^7$ is alkyl having 1 to 4 carbon atoms.

10. The compound according to claim 8, wherein $R^7$ is phenyl-$C_{1-4}$ alkyl.

11. The compound according to claim 1, wherein $R^1$ and $R^2$ are hydrogen.

12. The compound according to claim 1, wherein $R^1$ and $R^2$ are alkyl having 1 to 4 carbon atoms.

13. The compound according to claim 1, wherein X is

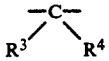

wherein $R^3$ and $R^4$ are defined as above.

14. The compound according to claim 13, wherein $R^3$ and $R^4$ are hydrogen.

15. The compound according to claim 13, wherein $R^3$ and $R^4$ are alkyl having 1 to 4 carbon atoms.

16. The compound according to claim 13, wherein $R^3$ and $R^4$ are phenyl.

17. The compound according to claim 13, wherein $R^3$ and $R^4$ are phenyl-$C_{1-4}$ alkyl.

18. The compound according to claim 1, wherein X is

19. The compound according to claim 1, wherein X is

wherein $R^5$ is defined as above.

20. The compound according to claim 19, wherein $R^5$ is hydrogen.

21. The compound according to claim 19, wherein $R^5$ is alkyl having 1 to 4 carbon atoms.

22. The compound according to claim 1, wherein Ring A is unsubstituted.

23. The compound according to claim 1, namely, 3-methylthio-11H-s-triazolo[3,4-b][3]benzazepine.

24. The compound according to claim 1, namely, 3-ethylthio-11H-s-triazolo[3,4-b][3]benzazepine.

25. The compound according to claim 1, namely, 6-methyl-3-methylthio-11H-s-triazolo[3,4-b][3]benzazepine.

26. The compound according to claim 1, namely, 11-methyl-3-methylthio-11H-s-triazolo[3,4-b][3]benzazepine.

27. The compound according to claim 1, namely, 8-chloro-3-methylthio-11H-s-triazolo[3,4-b][3]benzazepine.

28. The compound according to claim 1, namely, 3-methylthio-11-phenyl-11H-s-triazolo[3,4-b][3]benzazepine.

29. The compound according to claim 1, namely, 8-methyl-3-methylthio-11H-s-triazolo[3,4-b][3]benzazepine.

30. The compound according to claim 1, namely, 8-methoxy-3-methylthio-11H-s-triazolo[3,4-b][3]benzazepine.

31. The compound according to claim 1, namely, 9-methoxy-3-methylthio-11H-s-triazolo[3,4-b][3]benzazepine.

32. The compound according to claim 1, namely, 3-methylthio-11H-s-triazolo[3,4-b][3]benzazepin-11-one.

33. The compound according to claim 1, namely, 8-chloro-3-methylthio-11H-s-triazolo[3,4-b][3]benzazepin-11-one.

34. The compound according to claim 1, namely, 8-methyl-3-methylthio-11H-s-triazolo[3,4-b][3]benzazepin-11-one.

35. The compound according to claim 1, namely, 11-methylene-3-methylthio-11H-s-triazolo[3,4-b][3]benzazepine.

36. The compound according to claim 1, namely, 3-methylsulfinyl-11H-s-triazolo[3,4-b][3]benzazepine.

37. The compound according to claim 1, namely, 8-methyl-3-methylsulfinyl-11H-s-triazolo[3,4-b][3]benzazepine.

38. The compound according to claim 1, namely 8-chloro-3-methylsulfinyl-11H-s-triazolo[3,4-b][3] benzazepine.

39. The compound according to claim 1, namely, 8-methoxy-3-methylsulfinyl-11H-s-triazolo[3,4-b][3]benzazepine.

40. The compound according to claim 1, namely, 9-methoxy-3-methylsulfinyl-11H-s-triazolo[3,4-b][3]benzazepine.

41. The compound according to claim 1, namely, 3-ethylsulfinyl-11H-s-triazolo[3,4-b][3]benzazepine.

42. The compound according to claim 1, namely, 3-methylsulfonyl-11H-s-triazolo[3,4-b][3]benzazepine.

43. The compound according to claim 1, namely, 8-methyl-3-methylsulfonyl-11H-s-triazolo[3,4-b][3]benzazepine.

44. The compound according to claim 1, namely, 8-chloro-3-methylsulfonyl-11H-s-triazolo[3,4-b][3] benzazepine.

45. The compound according to claim 1, namely, 8-methoxy-3-methylsulfonyl-11H-s-triazolo[3,4-b][3]benzazepine.

46. The compound according to claim 1, namely, 9-methoxy-3-methylsulfonyl-11H-s-triazolo[3,4-b][3]benzazepine.

47. The compound according to claim 1, namely, 3-methylsulfonyl-11-phenyl-11H-s-triazolo[3,4-b][3]benzazepine.

48. The compound according to claim 1, namely, 11-methyl-3-methylsulfonyl-11H-s-triazolo[3,4-b][3]benzazepine.

49. The compound according to claim 1, namely, 3-methylsulfinyl-11H-s-triazolo[3,4-b][3]benzazepin-11-one.

50. The compound according to claim 1, namely, 11-methylene-3-methylsulfinyl-11H-s-triazolo[3,4-b][3] benzazepine.

51. The compound according to claim 1, namely, 3-methoxy-11H-s-triazolo[3,4-b][3]benzazepine.

52. The compound according to claim 1, namely, 3-ethoxy-11H-s-triazolo[3,4-b][3]benzazepine.

53. The compound according to claim 1, namely, 3-methoxy-8-methyl-11H-s-triazolo[3,4-b][3]benzazepine.

54. The compound according to claim 1, namely, 8-chloro-3-methoxy-11H-s-triazolo[3,4-b][3]benzazepine.

55. The compound according to claim 1, namely, 3,8-dimethoxy-11H-s-triazolo[3,4-b][3]benzazepine.

56. The compound according to claim 1, namely, 3,9-dimethoxy-11H-s-triazolo[3,4-b][3]benzazepine.

57. The compound according to claim 1, namely, 3-methoxy-11-phenyl-11H-s-triazolo[3,4-b][3]benzazepine.

58. The compound according to claim 1, namely, 3-methoxy-11-methyl-11H-s-triazolo[3,4-b][3]benzazepine.

59. The compound according to claim 1, namely, 3-methoxy-11-methylene-11H-s-triazolo[3,4-b][3]benzazepine.

60. The compound according to claim 1, namely, 3-methoxy-11H-s-triazolo[3,4-b][3]benzazepin-11-one.

61. A pharmaceutical composition which comprises (A) as the active ingredient, an analgesically, antiinflammatory- or muscle relaxant-effective amount of at least one compound selected from the group consisting of compounds of the formula

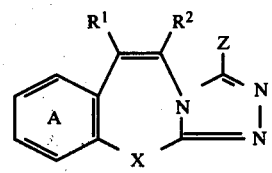

wherein $R^1$ and $R^2$ are hydrogen or alkyl having 1 to 4 carbon atoms, X is

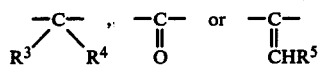

wherein $R^3$ and $R^4$ are hydrogen, alkyl having 1 to 4 carbon atoms, phenyl or phenyl-$C_{1-4}$ alkyl, and $R^5$ is hydrogen or alkyl having 1 to 4 carbon atoms, Z is —$SR^6$, —$S(O)nR^6$ or —$OR^7$ wherein $R^6$ and $R^7$ are alkyl having 1 to 4 carbon atoms or phenyl-$C_{1-4}$-alkyl, and n is 1 or 2, and Ring A is unsubstituted or substituted with from one to four of halogen, lower alkyl, lower alkoxy and trifluoromethyl, and physiologically acceptable salts thereof, and (B) a pharmaceutically acceptable carrier therefor.

* * * * *